(12) United States Patent
Harrington et al.

(10) Patent No.: US 7,244,726 B2
(45) Date of Patent: Jul. 17, 2007

(54) HETEROCYCLIC COMPOUNDS POSSESSING AFFINITY AT 5HT$_1$-TYPE RECEPTORS AND USE THEREOF IN THERAPY

(75) Inventors: Frank P Harrington, Harlow (GB); Paul W Smith, Harlow (GB); Simon E Ward, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 329 days.

(21) Appl. No.: 10/504,109

(22) PCT Filed: Feb. 17, 2003

(86) PCT No.: PCT/EP03/01711

§ 371 (c)(1),
(2), (4) Date: Aug. 10, 2004

(87) PCT Pub. No.: WO03/068772

PCT Pub. Date: Aug. 21, 2003

(65) Prior Publication Data

US 2005/0085458 A1 Apr. 21, 2005

(30) Foreign Application Priority Data

Feb. 18, 2002 (GB) ................... 0203804.0

(51) Int. Cl.
*C07D 413/10* (2006.01)
*A61K 31/538* (2006.01)
(52) U.S. Cl. .................... 514/230.5; 544/105
(58) Field of Classification Search ............... 544/105; 514/230.5
See application file for complete search history.

(56) References Cited

FOREIGN PATENT DOCUMENTS

| EP | 0 900 792 | 3/1999 |
|---|---|---|
| WO | WO 95 28400 | 10/1995 |
| WO | WO 97 45419 | 12/1997 |
| WO | WO 99 51592 | 10/1999 |
| WO | WO 00 40581 | 7/2000 |
| WO | WO 02 34754 | 5/2002 |

*Primary Examiner*—Kahsay Habte
(74) *Attorney, Agent, or Firm*—Kathryn L. Sieburth; Mary E. McCarthy; Charles M. Kinzig

(57) ABSTRACT

Compounds of formula (I) and pharmaceutically acceptable salts thereof are disclosed:

wherein A is optionally substituted phenyl, naphthyl, indolyl, quinolinyl, quinazolinyl, indazolyl, isoquinolinyl or benzofuranyl; b is 1, 2 or 3 and c is 1, 2 or 3, wherein b+c is 2, 3, 4 or 5; X is carbon, Y is CH, is a double bond and e is 0; or X is carbon, Y is CH$_2$ or oxygen, is a single bond and e is 1; or X is nitrogen, Y is CH$_2$, is a single bond and e is 0; R1 is hydrogen, cyano, halogen, C$_{1-6}$alkyl, C$_{1-6}$alkoxy, C$_{1-6}$alkoxyC$_{1-6}$alkyl, NHCOCH$_3$ or OCONR5R6, wherein R5 and R6 are independently hydrogen or C$_{1-6}$alkyl; R2 is halogen, cyano or C$_{1-6}$alkoxy; d is 0, 1, 2 or 3; R3 is hydrogen, C$_{1-6}$alkyl, C$_{1-6}$alkanoyl, fluoroC$_{1-6}$alkanoyl, C$_{1-6}$alkylsulfonyl, fluoroC$_{1-6}$alkylsulfonyl, carbamoyl, C$_{1-6}$alkylcarbamoyl or arylC$_{1-6}$alkyl; and R4, together with the nitrogen atom to which it is attached, forms an optionally substituted 5 to 7 membered heterocyclic group fused to the benzene ring, provided that when a compound of formula (I) has the following structure:

wherein A, b, c, R1, e, X, Y, R2 and d are as defined above and R3 is hydrogen, C$_{1-6}$alkyl or arylC$_{1-6}$alkyl, then (i) X is carbon, Y is CH and is a double bond; or (ii) b and c are both 1; or (iii) the carbon atom adjacent to the oxo-substituted carbon atom in the morpholinyl ring, marked "★", is substituted. Methods of preparing the compounds and uses of the compounds in therapy, in particular for a CNS disorder such as depression or anxiety, are also disclosed.

11 Claims, No Drawings

HETEROCYCLIC COMPOUNDS POSSESSING AFFINITY AT 5HT$_1$ -TYPE RECEPTORS AND USE THEREOF IN THERAPY

The present invention relates to novel compounds, processes for their preparation, pharmaceutical compositions containing the same and their use as medicaments in the treatment of CNS and other disorders.

PCT/EP01/12344 (WO02/34754) discloses benzoxazinone derivatives which are useful in the treatment of CNS disorders.

A novel series of compounds has now been found that possess high affinity for 5-HT$_1$ type receptors and/or are 5-HT reuptake inhibitors. The present invention therefore provides, in a first aspect, a compound of formula (I) or a pharmaceutically acceptable salt thereof:

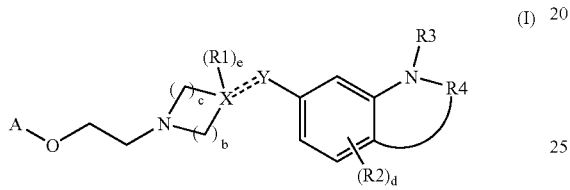

wherein:
A is optionally substituted phenyl, naphthyl, indolyl, quinolinyl, quinazolinyl, indazolyl, isoquinolinyl or benzofuranyl,
b is 1, 2 or 3 and c is 1, 2 or 3, wherein b+c is 2, 3, 4 or 5;
X is carbon, Y is CH,

:::::

is a double bond and e is 0; or X is carbon, Y is CH$_2$ or oxygen,

:::::

is a single bond and e is 1; or X is nitrogen, Y is CH$_2$,

:::::

is a single bond and e is 0;
R1 is hydrogen, cyano, halogen, C$_{1-6}$alkyl, C$_{1-6}$alkoxy, C$_{1-6}$alkoxyC$_{1-6}$alkyl, NHCOCH$_3$ or OCONR5R6, wherein R5 and R6 are independently hydrogen or C$_{1-6}$alkyl;
R2 is halogen, cyano or C$_{1-6}$alkoxy;
d is 0, 1, 2 or 3;
R3 is hydrogen, C$_{1-6}$alkyl, C$_{1-6}$alkanoyl, fluoroC$_{1-6}$alkanoyl, C$_{1-6}$alkylsulfonyl, fluoroC$_{1-6}$alkylsulfonyl, carbamoyl, C$_{1-6}$alkylcarbamoyl or arylC$_{1-6}$alkyl; and
R4, together with the nitrogen atom to which it is attached, forms an optionally substituted 5 to 7 membered heterocyclic group fused to the benzene ring, provided that when a compound of formula (I) has the following structure:

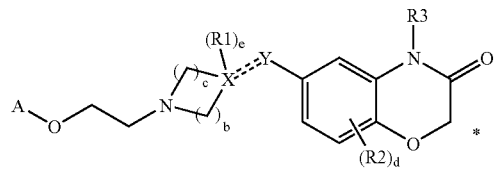

wherein A, b, c, R1, e, X, Y, R2 and d are as defined above and R3 is hydrogen, C$_{1-6}$alkyl or arylC$_{1-6}$alkyl, then
 (i) X is carbon, Y is CH and

:::::

is a double bond; or
 (ii) b and c are both 1; or
 (iii) the carbon atom adjacent to the oxo-substituted carbon atom in the morpholinyl ring, marked "★", is substituted.

The term "halogen" and its abbreviation "halo" refer to fluorine, chlorine, bromine or iodine.

The term "C$_{1-6}$alkyl" refers to an alkyl group having from one to six carbon atoms, in all isomeric forms, such as methyl, ethyl, propyl, isopropyl, butyl, isobutyl, sec-butyl, tert-butyl, pentyl, neopentyl, sec-pentyl, n-pentyl, isopentyl, tert-pentyl and hexyl.

The term "C$_{1-6}$alkoxy" refers to a straight chain or branched chain alkoxy (or "alkyloxy") group having from one to six carbon atoms, such as methoxy, ethoxy, propoxy, isopropoxy, butoxy, isobutoxy, sec-butoxy, tert-butoxy, pentoxy, neopentoxy, sec-pentoxy, n-pentoxy, isopentoxy, tert-pentoxy and hexoxy.

The term "C$_{1-6}$alkanoyl" refers to an alkanoyl group having from 1 to 6 carbon atoms, such as methanoyl (or "formyl"), ethanoyl (or "acetyl"), propanoyl, isopropanoyl, butanoyl, isobutanoyl, sec-butanoyl, pentanoyl, neopentanoyl, sec-pentanoyl, isopentanoyl, tertpentanoyl and hexanoyl.

The term "fluoroC$_{1-6}$alkanoyl" refers to a fluorine-substituted C$_{1-6}$alkanoyl group such as CF$_3$CO. The term "fluoroC$_{1-6}$alkylsulfonyl" refers to a fluorine-substituted C$_{1-6}$alkylsulfonyl group such as CF$_3$SO$_2$.

The term "carbamoyl" refers to the group H$_2$NCO. The term "C$_{1-6}$alkylcarbamoyl" refers to a group having the formula (C$_{1-6}$alkyl)HNCO, such as CH$_3$NHCO.

The term "aryl", whether alone or as part of another group, is intended, unless otherwise stated, to denote an aromatic carbocyclic or heterocyclic group such as phenyl, naphthyl, pyridyl or pyrazinyl, optionally substituted by one or more, preferably 1 to 3, halogen, C$_{1-6}$alkyl, CF$_3$, cyano, hydroxy, C$_{1-6}$alkanoyl, or C$_{1-6}$alkoxy. Where used herein the term naphthyl, whether alone or as part of another group, is intended, unless otherwise stated, to denote both 1-naphthyl and 2-naphthyl groups.

The term "oxo" refers to the group "=O".

The term "optionally substituted 5 to 7 membered heterocyclic group" refers to an optionally substituted saturated or non-saturated ring containing at least one nitrogen atom and optionally a further 1 or 2 heteroatoms selected from nitrogen, sulphur or oxygen, the ring consisting of a total of 5 to 7 atoms. Examples of such heterocyclic groups include pyrrolidinyl, imidazolidinyl, pyrazolidinyl, oxazolidinyl, isothiazolidinyl, thiazolidinyl, pyrrolyl, pyrrolinyl, pyrazolinyl, imidazolyl, pyrazolyl, isothiazolyl, thiazolyl, piperidyl, piperazinyl, morpholinyl, thiomorpholinyl, pyridyl, pyridazinyl, pyrimidinyl, pyrazinyl, azepinyl and azepanyl. Examples of groups formed when the optionally substituted 5 to 7 membered heterocyclic group in formula (I) is fused to the benzene ring include quinoxalinyl, benzoxazinyl and quinolinyl. The heterocyclic group may be substituted by one or more, preferably 1 to 3, substituents, which may be the same or different, and which is selected from the following group: oxo, $C_{1-6}$alkyl, cyano, $CF_3$, $C_{1-6}$alkoxy and $C_{1-6}$alkanoyl.

The term "$C_{3-7}$cycloalkyl$C_{1-6}$alkoxy" refers to a cycloalkyl group consisting of from 3 to 7 carbon atoms (for example cyclopropane, cyclobutane, cyclopentane, cyclohexane and cycloheptane) attached to an aryl$C_{1-6}$alkoxy group.

When d is two or more, the two or more R2 groups may be the same or different.

A is optionally substituted phenyl, naphthyl, indolyl, quinolinyl, quinazolinyl, indazolyl, isoquinolinyl or benzofuranyl. These groups may be attached to the oxygen atom at any suitable position. These groups may be substituted by 1 to 4 substituents, which may be the same or different, and which are selected from the following group: halogen, hydroxy, cyano, $CF_3$, $C_{1-6}$alkyl, $C_{1-6}$alkoxy, $C_{1-6}$alkoxy$C_{1-6}$alkyl, $C_{3-7}$cycloalkyl$C_{1-6}$alkoxy, $C_{1-6}$alkanoyl, $C_{1-6}$alkylsulfonyl, $C_{1-6}$alkylsulfinyl, $C_{1-6}$alkylsulfonyloxy, $C_{1-6}$alkylsulfonyl$C_{1-6}$alkyl, $C_{1-6}$alkylsulfonamido, $C_{1-6}$alkylamido, $C_{1-6}$alkylsulfonamido$C_{1-6}$alkyl and $C_{1-6}$alkylamido$C_{1-6}$alkyl. Preferred optional substituents for A are $C_{1-6}$alkyl, cyano, $CF_3$, $C_{1-6}$alkoxy and $C_{1-6}$alkanoyl.

Preferably A is quinolinyl or quinazolinyl. Most preferably, A is 5-(2-methyl)quinolinyl or 5-(2-methyl)quinazolinyl.

Preferably R2 is fluoro.
Preferably d is 0, 1 or 2.
Preferably Y is $CH_2$ or CH.
Preferably both b and c are 2.
Preferably R3 is hydrogen, $C_{1-6}$alkyl (particularly methyl, ethyl or propyl) or $C_{1-6}$alkylsulfonyl.
Preferably, the 5 to 7 membered heterocyclic group formed by R4 is a 5 or 6 membered ring, such as pyrazine, morpholine, oxazolidine, piperidine or pyrrolidine.
Preferably, the 5 to 7 membered heterocyclic group formed by R4, together with the phenyl ring to which it is fused, forms an unsubstituted benzoxazinyl group, to form compounds having the following formula:

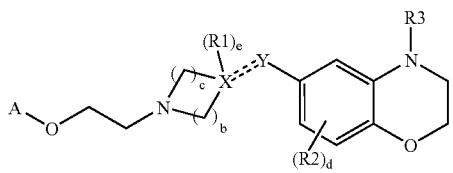

wherein A, R1, R2, R3, b, c, d, e, X, Y and
===== have the same meanings as defined for formula (I). Preferred features of formula (I) apply mutatis mutandis.

International patent application no. PCT/EP01/12344, the contents of which are herein incorporated by reference as though fully set forth, discloses certain benzoxazinone derivatives which are useful in the treatment and/or prophylaxis of CNS and other disorders. In particular, PCT/EP01/12344 discloses the following compounds which are outside the scope of the present invention:
1. 6-(4-(1-(2-(4-1H-Indolyloxy)ethyl)piperidinyl)oxy)-4H-benzo[1,4]oxazin-3-one (compound E1 in PCT/EP01/12344)
2. 6-(4-(1-(2-(4-(2-Cyano)-1H-indolyloxy)ethyl)piperidinyl)oxy)-4H-benzo[1,4]oxazin-3-one (E2)
3. 6-(4-(1-(2-(5-Quinolinyloxy)ethyl)piperidinyl)methyl)-4H-benzo[1,4]oxazin-3-one (E4)
4. 6-(4-(1-(2-(1-naphthyloxy)ethyl)piperidinyl)oxy)-4-methyl-4H-benzo[1,4]oxazin-3-one (E8)
5. 6-(4-(1-(2-(2,3-dichlorophenoxy)ethyl)piperidinyl)oxy)-4H-benzo[1,4]oxazin-3-one (E12)
6. 6-(4-(1-(2-(3-bromophenoxy)ethyl)piperidinyl)oxy)-4H-benzo[1,4]oxazin-3-one (E14)
7. 6-(4-(1-(2-(3-methylphenoxy)ethyl)piperidinyl)oxy)-4H-benzo[1,4]oxazin-3-one (E15)
8. 6-(4-(1-(2-(1-naphthyloxy)ethyl)piperidinyl)oxy)-4H-benzo[1,4]oxazin-3-one (E17)
9. 6-(4-(1-(2-(3-trifluoromethylphenoxy)ethyl)piperidinyl)oxy)-4H-benzo[1,4]oxazin-3-one (E18)
10. 6-(4-(1-(2-((3-ethyl-4-chloro)phenoxy)ethyl)piperidinyl)oxy)-4H-benzo[1,4]oxazin-3-one (E19)
11. 6-(4-(1-(2-(2-propylphenoxy)ethyl)piperidinyl)oxy)-4H-benzo[1,4]oxazin-3-one (E20)
12. 6-(4-(1-(2-(5-quinolinyloxy)ethyl)piperidinyl)oxy)-4H-benzo[1,4]oxazin-3-one (E22)
13. 6-(4-(1-(2-(1-isoquinolinyloxy)ethyl)piperidinyl)oxy)-4H-benzo[1,4]oxazin-3-one (E24)
14. 6-(4-(1-(2-(8-quinolinyloxy)ethyl)piperidinyl)oxy)-4H-benzo[1,4]oxazin-3-one (E26)
15. 6-(4-(1-(2-(7-benzo[b]furanyloxy)ethyl)piperidinyl)oxy)-4H-benzo[1,4]oxazin-3-one (E27)
16. 6-(4-(1-(2-(7-benzo[b]furanyloxy)ethyl)piperidinyl)oxy)-4-methyl-4H-benzo[1,4]oxazin-3-one (E30)
17. 6-(4-(1-(2-(7-(2-methyl)benzo[b]furanyloxy)ethyl)piperidinyl)oxy)-4-methyl-4H-benzo[1,4]oxazin-3-one (E38)
18. 6-(4-(1-(2-(5-quinolinyloxy)ethyl)piperidinyl)oxy)-4-methyl-4H-benzo[1,4]oxazin-3-one (E41)
19. 6-(4-(1-(2-(2-cyanophenoxy)ethyl)piperidinyl)methyl)-4H-benzo[1,4]oxazin-3-one (E45)
20. 6-(4-(1-(2-(4-indolyloxy)ethyl)piperidinyl)methyl)-4H-benzo[1,4]oxazin-3-one (E48)
21. 6-(4-(1-(2-(4-indolyloxy)ethyl)piperidinyl)methyl)-4-methyl-4H-benzo[1,4]oxazin-3-one (E52)
22. 6-(4-(1-(2-(1-naphthyloxy)ethyl)piperidinyl)methyl)-4H-benzo[1,4]oxazin-3-one (E53)
23. 6-(4-(1-(2-(2-isopropoxyphenoxy)ethyl)piperidinyl)methyl)-4H-benzo[1,4]oxazin-3-one (E54)
24. 6-(4-(1-(2-(4-benzo[b]furanyl)ethyl)piperidinyl)methyl)-4H-benzo[1,4]oxazin-3-one (E57)
25. 6-(3-(1-(3-(1-naphthyloxy)ethyl)pyrrolidinyl)oxy)-4H-benzo[1,4]oxazin-3-one (E83)
26. 6-(4-(1-(2-(4-indolyloxy)ethyl)piperazinyl)methyl)-4H-benzo[1,4]oxazin-3-one (E95)
27. 6-(4-(1-(2-(1-naphthyloxy)ethyl)piperazinyl)methyl)-4H-benzo[1,4]oxazin-3-one (E96)
28. 6-(4-(1-(2-(5-quinolinyloxy)ethyl)piperazinyl)methyl)-4H-benzo[1,4]oxazin-3-one (E104)
29. 6-(4-(1-(2-(5-(2-Methyl)quinolinyloxy)ethyl)piperidinyl)methyl)-4H-benzo[1,4]oxazin-3-one (E108)

30. 6-(4-(1-(2-(5-(2-Methyl)quinolinyloxy)ethyl)piperidinyl)methyl)-4H-benzo[1,4]oxazin-3-one dihydrochloride (E108a)
31. 6-(4-(1-(2-(5-(3-Methyl)quinolinyloxy)ethyl)piperidinyl)methyl)-4H-benzo[1,4]oxazin-3-one (E109)
32. 6-(4-(1-(2-(4-(1H)-Indazolyloxy)ethyl)piperidinyl)methyl)-4H-benzo[1,4]oxazin-3-one (E112)
33. 6-(4-(1-(2-(5-(2-Methyl)quinolinyloxy)ethyl)piperidinyl)oxy)-4H-benzo[1,4]oxazin-3-one (E113)
34. 4-Methyl-6-(4-(1-(2-(5-(2-methyl)quinolinyloxy)ethyl)piperidinyl)oxy)-4H-benzo[1,3]oxazin-3-one (E114)
35. 6-(4-(1-(2-(5-(2-Methyl)quinolinyloxy)ethyl)piperazinyl)methyl)-4H-benzo[1,4]oxazin-3-one (E115)
36. 4-Methyl-6-(4-(1-(2-(5-(2-methyl)quinolinyloxy)ethyl)piperidinyl)methyl)-4H-benzo[1,4]oxazin-3-one (E120)
37. 6-(4-(1-(2-(5-(8-Chloro-2-methyl)quinolinyloxy)ethyl)piperidinyl)methyl)-4H-benzo[1,4]oxazin-3-one (E121)
38. 6-(4-(1-(2-(5-(8-Chloro-2-methyl)quinolinyloxy)ethyl)piperidinyl)methyl)-4-methyl-4H-benzo[1,4]oxazin-3-one (E123)
39. 6-(4-(1-(2-(5-(8-Fluoro-2-methyl)quinolinyloxy)ethyl)piperidinyl)methyl)-4H-benzo[1,4]oxazin-3-one (E124)
40. 6-(4-(1-(2-(5-(8-Fluoro-2-methyl)quinolinyloxy)ethyl)piperidinyl)methyl)-4-methyl-4H-benzo[1,4]oxazin-3-one (E125)
41. 6-(4-(1-(2-(5-(8-Fluoro-2-methyl)quinolinyloxy)ethyl)piperidinyl)oxy)-4H-benzo[1,4]oxazin-3-one (E126)
42. 6-(4-(1-(2-(5-(8-Fluoro-2-methyl)quinolinyloxy)ethyl)piperidinyl)oxy)-4-methyl-4H-benzo[1,4]oxazin-3-one (E127)
43. 6-(4-(1-(2-(5-(7-Chloro-2-methyl)quinolinyloxy)ethyl)piperidinyl)methyl)-4H-benzo[1,4]oxazin-3-one (E128)
44. 6-(4-(1-(2-(5-(7-Chloro-2-methyl)quinolinyloxy)ethyl)piperidinyl)methyl)-4-methyl-4H-benzo[1,4]oxazin-3-one (E129)
45. 6-(4-(1-(2-(5-(7-Chloro-2-methyl)quinolinyloxy)ethyl)piperidinyl)oxy)-4H-benzo[1,4]oxazin-3-one (E130)
46. 6-(4-(1-(2-(5-(7-Chloro-2-methyl)quinolinyloxy)ethyl)piperidinyl)oxy)-4-methyl-4H-benzo[1,4]oxazin-3-one (E131)
47. 6-(4-(1-(2-(5-(7-Chloro-2-methyl)quinolinyloxy)ethyl)piperazinyl)methyl)-4H-benzo[1,4]oxazin-3-one (E132)
48. 6-(4-(1-(2-(5-(2-Methyl)quinolinyloxy)ethyl)piperidinyl)methyl)-4-(2-propyl)-4H-benzo[1,4]oxazin-3-one (E135)
49. 6-(4-(1-(2-(5-(2-Methyl)quinazolinyloxy)ethyl)piperidinyl)methyl)-4H-benzo[1,4]-oxazin-3-one (E136)
50. 6-(4-(1-(2-(5-(7-Fluoro-2-methyl)quinolinyloxy)ethyl)piperidinyl)methyl)-4H-benzo[1,4]oxazin-3-one (E137)
51. 6-(4-(1-(2-(4-benzofuranyloxy)ethyl)piperidinyl)oxy)-4H-benzo[1,4]oxazin-3-one (E138)
52. 6-(4-(1-(2-(4-benzofuranyloxy)ethyl)piperidinyl)oxy)-4-methyl-4H-benzo[1,4]oxazin-3-one (E139)
53. 6-(4-(1-(2-(1-isoquinolinyloxy)ethyl)piperidinyl)oxy)-4-methyl-4H-benzo[1,4]oxazin-3-one (E140)
54. 6-(4-(1-(2-(5-(8-chloro-2-methyl)quinolinyloxy)ethyl)piperidinyl)oxy)-4-methyl-4H-benzo[1,4]oxazin-3-one (E141)
55. 6-(4-(1-(2-(1-isoquinolinyloxy)ethyl)piperidinyl)methyl)-4H-benzo[1,4]oxazin-3-one (E142)
56. 6-(4-(1-(2-(4-benzofuranyloxy)ethyl)piperazinyl)methyl)-4H-benzo[1,4]oxazin-3-one (E144)
57. 6-(4-(1-(2-(1-isoquinolinyloxy)ethyl)piperazinyl)methyl)-4H-benzo[1,4]oxazin-3-one (E145)
58. 6-{1-[2-(6-Fluoro-2-methyl-quinolin-5-yloxy)-ethyl]-piperidin-4-ylmethyl}-4H-benzo[1,4]oxazin-3-one (E147)
59. 6-{4-[2-(6-Fluoro-2-methyl-quinolin-5-yloxy)-ethyl]-piperazin-1-ylmethyl}-4H-benzo[1,4]oxazin-3-one (E148)
60. 6-{1-[2-(7,8-Difluoro-2-methyl-quinolin-5-yloxy)-ethyl]-piperidin-4-ylmethyl}4H-benzo[1,4]oxazin-3-one (E149)
61. 6-{4-[2-(7,8-Difluoro-2-methyl-quinolin-5-yloxy)-ethyl]-piperazin-1-ylmethyl}4H-benzo[1,4]oxazin-3-one (E150)
62. 6-{-[2-(7-Iodo-2-methyl-quinolin-5-yloxy)-ethyl]-piperidin-4-ylmethyl}-4H-benzo[1,4]oxazin-3-one (E151)
63. 2-Methyl-5-{2-[4-(3-oxo-3,4-dihydro-2H-benzo[1,4]oxazin-6-ylmethyl)-piperidin-1-yl]-ethoxy}-quinoline-7-carbonitrile (E152)
64. 6-(4-(1-(2-(5-(2-Methyl)quinolinyloxy)ethyl)piperazinyl)methyl)-4-ethyl-4H-benzo[1,4]oxazin-3-one (E153)
65. 6-(4-(1-(2-(5-(2-Methyl)quinolinyloxy)ethyl)piperazinyl)methyl)-4-(1-propyl)-4H-benzo[1,4]oxazin-3-one (E154)
66. 6-(4-(1-(2-(5-(2-Methyl)quinolinyloxy)ethyl)piperazinyl)methyl)-4-(1-butyl)-4H-benzo[1,4]oxazin-3-one (E155)
67. 6-(4-(1-(2-(5-(2-Methyl)quinolinyloxy)ethyl)piperazinyl)methyl)-4-(2-methyl-1-propyl)-4H-benzo[1,4]oxazin-3-one (E156)
68. 6-(4-(1-(2-(5-(2-Methyl)quinolinyloxy)ethyl)piperazinyl)methyl)-4-benzyl-4H-benzo[1,4]oxazin-3-one (E157)
69. 6-(4-(1-(2-(5-(2-Methyl)quinolinyloxy)ethyl)piperazinyl)methyl)-4-phenethyl-4H-benzo[1,4]oxazin-3-one (E158)
70. 4-Ethyl-6-{1-[2-(2-methyl-quinolin-5-yloxy)-ethyl]-piperidin-4-ylmethyl}-4H-benzo[1,4]oxazin-3-one (E159)
71. 7,8-Difluoro-6-(4-(1-(2-(5-(2-methyl)quinolinyloxy)ethyl)piperazinyl)methyl)-4H-benzo[1,4]oxazin-3-one (E160)
72. 8-Fluoro-6-(4-(1-(2-(5-(2-methyl)quinolinyloxy)ethyl)piperidinyl)methyl)-4H-benzo[1,4]oxazin-3-one (E161)
73. 8-Fluoro-4-methyl-6-(4-(1-(2-(5-(2-methyl)quinolinyloxy)ethyl)piperidinyl)methyl)-4H-benzo[1,4]oxazin-3-one (E162)
74. 7-Fluoro-6-(4-(1-(2-(5-(2-methyl)quinolinyloxy)ethyl)piperidinyl)methyl)-4H-benzo[1,4]oxazin-3-one (E163)
75. 8-Fluoro-6-(4-(1-(2-(5-(2-Methyl)quinazolinyloxy)ethyl)piperidinyl)methyl)-4H-benzo[1,4]-oxazin-3-one (E164)
76. 7-Fluoro-6-(4-(1-(2-(5-(2-Methyl)quinazolinyloxy)ethyl)piperidinyl)methyl)-4H-benzo[1,4]-oxazin-3-one (E165)
77. 8-Fluoro-6-(4-(1-(2-(5-(7-Chloro-2-methyl)quinolinyloxy)ethyl)piperidinyl)methyl)-4H-benzo[1,4]oxazin-3-one (E166)
78. 7-Fluoro-6-(4-(1-(2-(5-(7-Chloro-2-methyl)quinolinyloxy)ethyl)piperidinyl)methyl)-4H-benzo[1,4]oxazin-3-one (E167).

Thus, the present invention provides a compound of formula (I) or a pharmaceutically acceptable salt thereof:

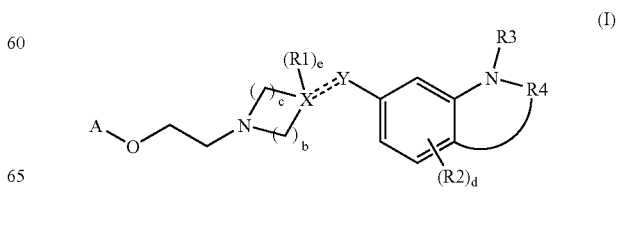

wherein:

A is optionally substituted phenyl, naphthyl, indolyl, quinolinyl, quinazolinyl, indazolyl, isoquinolinyl or benzofuranyl, b is 1, 2 or 3 and c is 1, 2 or 3, wherein b+c is 2, 3, 4 or 5;

X is carbon, Y is CH,

:::::

is a double bond and e is 0; or X is carbon, Y is $CH_2$ or oxygen,

:::::

is a single bond and e is 1; or X is nitrogen, Y is $CH_2$,

:::::

is a single bond and e is 0;

R1 is hydrogen, cyano, halogen, $C_{1-6}$alkyl, $C_{1-6}$alkoxy, $C_{1-6}$alkoxy$C_{1-6}$alkyl, NHCOCH$_3$ or OCONR5R6, wherein R5 and R6 are independently hydrogen or $C_{1-6}$alkyl;

R2 is halogen, cyano or $C_{1-6}$alkoxy;

d is 0, 1, 2 or 3;

R3 is hydrogen, $C_{1-6}$alkyl, $C_{1-6}$alkanoyl, fluoro$C_{1-6}$alkanoyl, $C_{1-6}$alkylsulfonyl, fluoro$C_{1-6}$alkylsulfonyl, carbamoyl, $C_{1-6}$alkylcarbamoyl or aryl$C_{1-6}$alkyl; and R4, together with the nitrogen atom to which it is attached, forms an optionally substituted 5 to 7 membered heterocyclic group fused to the benzene ring;

excluding the following:

6-(4-(1-(2-(4-1H-Indolyloxy)ethyl)piperidinyl)oxy)-4H-benzo[1,4]oxazin-3-one 6-(4-(1-(2-(4-(2-Cyano)-1H-indolyloxy)ethyl)piperidinyl)oxy)-4H-benzo[1,4]oxazin-3-one 6-(4-(1-(2-(5-Quinolinyloxy)ethyl)piperidinyl)methyl)-4H-benzo[1,4]oxazin-3-one 6-(4-(1-(2-(1-naphthyloxy)ethyl)piperidinyl)oxy)-4-methyl-4H-benzo[1,4]oxazin-3-one 6-(4-(1-(2-(2,3-dichlorophenoxy)ethyl)piperidinyl)oxy)-4H-benzo[1,4]oxazin-3-one 6-(4-(1-(2-(3-bromophenoxy)ethyl)piperidinyl)oxy)-4H-benzo[1,4]oxazin-3-one 6-(4-(1-(2-(3-methylphenoxy)ethyl)piperidinyl)oxy)-4H-benzo[1,4]oxazin-3-one 6-(4-(1-(2-(1-naphthyloxy)ethyl)piperidinyl)oxy)-4H-benzo[1,4]oxazin-3-one 6-(4-(1-(2-(3-trifluoromethylphenoxy)ethyl)piperidinyl)oxy)-H-benzo[1,4]oxazin-3-one 6-(4-(1-(2-((3-ethyl-4-chloro)phenoxy)ethyl)piperidinyl)oxy)-4H-benzo[1,4]oxazin-3-one 6-(4-(1-(2-(2-propylphenoxy)ethyl)piperidinyl)oxy)-4H-benzo[1,4]oxazin-3-one 6-(4-(1-(2-(5-quinolinyloxy)ethyl)piperidinyl)oxy)-4H-benzo[1,4]oxazin-3-one 6-(4-(1-(2-(1-isoquinolinyloxy)ethyl)piperidinyl)oxy)-4H-benzo[1,4]oxazin-3-one 6-(4-(1-(2-(8-quinolinyloxy)ethyl)piperidinyl)oxy)-4H-benzo[1,4]oxazin-3-one 6-(4-(1-(2-(7-benzo[b]furanyloxy)ethyl)piperidinyl)oxy)-4H-benzo[1,4]oxazin-3-one 6-(4-(1-(2-(7-benzo[b]furanyloxy)ethyl)piperidinyl)oxy)-4-methyl-4H-benzo[1,4]oxazin-3-one 6-(4-(1-(2-(7-(2-methyl)benzo[b]furanyloxy)ethyl)piperidinyl)oxy)-4-methyl-4H-benzo[1,4]oxazin-3-one 6-(4-(1-(2-(5-quinolinyloxy)ethyl)piperidinyl)oxy)-4-methyl-4H-benzo[1,4]oxazin-3-one 6-(4-(1-(2-(2-cyanophenoxy)ethyl)piperidinyl)methyl)-4H-benzo[1,4]oxazin-3-one 6-(4-(1-(2-(4-indolyloxy)ethyl)piperidinyl)methyl)-4H-benzo[1,4]oxazin-3-one 6-(4-(1-(2-(4-indolyloxy)ethyl)piperidinyl)methyl)-4-methyl-4H-benzo[1,4]oxazin-3-one 6-(4-(1-(2-(1-naphthyloxy)ethyl)piperidinyl)methyl)-4H-benzo[1,4]oxazin-3-one 6-(4-(1-(2-(2-isopropoxyphenoxy)ethyl)piperidinyl)methyl)-4H-benzo[1,4]oxazin-3-one 6-(4-(1-(2-(4-benzo[b]furanyl)ethyl)piperidinyl)methyl)-4H-benzo[1,4]oxazin-3-one 6-(3-(1-(3-(1-naphthyloxy)ethyl)pyrrolidinyl)oxy)-4H-benzo[1,4]oxazin-3-one 6-(4-(1-(2-(4-indolyloxy)ethyl)piperazinyl)methyl)-4H-benzo[1,4]oxazin-3-one 6-(4-(1-(2-(1-naphthyloxy)ethyl)piperazinyl)methyl)-4H-benzo[1,4]oxazin-3-one 6-(4-(1-(2-(5-quinolinyloxy)ethyl)piperazinyl)methyl)-4H-benzo[1,4]oxazin-3-one 6-(4-(1-(2-(5-(2-Methyl)quinolinyloxy)ethyl)piperidinyl)methyl)-4H-benzo[1,4]oxazin-3-one 6-(4-(1-(2-(5-(2-Methyl)quinolinyloxy)ethyl)piperidinyl)methyl)-4H-benzo[1,4]oxazin-3-one dihydrochloride 6-(4-(1-(2-(5-(3-Methyl)quinolinyloxy)ethyl)piperidinyl)methyl)-4H-benzo[1,4]oxazin-3-one 6-(4-(1-(2-(4-(1H)-Indazolyloxy)ethyl)piperidinyl)methyl)-4H-benzo[1,4]oxazin-3-one 6-(4-(1-(2-(5-(2-Methyl)quinolinyloxy)ethyl)piperidinyl)oxy)-4H-benzo[1,4]oxazin-3-one 4-Methyl-6-(4-(1-(2-(5-(2-methyl)quinolinyloxy)ethyl)piperidinyl)oxy)-4H-benzo[1,3]oxazin-3-one 6-(4-(1-(2-(5-(2-Methyl)quinolinyloxy)ethyl)piperazinyl)methyl)-4H-benzo[1,4]oxazin-3-one 4-Methyl-6-(4-(1-(2-(5-(2-methyl)quinolinyloxy)ethyl)piperidinyl)methyl)-4H-benzo[1,4]oxazin-3-one 6-(4-(1-(2-(5-(8-Chloro-2-methyl)quinolinyloxy)ethyl)piperidinyl)methyl)-4H-benzo[1,4]oxazin-3-one 6-(4-(1-(2-(5-(8-Chloro-2-methyl)quinolinyloxy)ethyl)piperidinyl)methyl)-4-methyl-4H-benzo[1,4]oxazin-3-one 6-(4-(1-(2-(5-(8-Fluoro-2-methyl)quinolinyloxy)ethyl)piperidinyl)methyl)-4H-benzo[1,4]oxazin-3-one 6-(4-(1-(2-(5-(8-Fluoro-2-methyl)quinolinyloxy)ethyl)piperidinyl)methyl)-4-methyl-4H-benzo[1,4]oxazin-3-one 6-(4-(1-(2-(5-(8-Fluoro-2-methyl)quinolinyloxy)ethyl)piperidinyl)oxy)-4H-benzo[1,4]oxazin-3-one 6-(4-(1-(2-(5-(8-Fluoro-2-methyl)quinolinyloxy)ethyl)piperidinyl)oxy)-4-methyl-4H-benzo[1,4]oxazin-3-one 6-(4-(1-(2-(5-(7-Chloro-2-methyl)quinolinyloxy)ethyl)piperidinyl)methyl)-4H-benzo[1,4]oxazin-3-one 6-(4-(1-(2-(5-(7-Chloro-2-methyl)quinolinyloxy)ethyl)piperidinyl)methyl)-4-methyl-4H-benzo[1,4]oxazin-3-one 6-(4-(1-(2-(5-(7-Chloro-2-methyl)quinolinyloxy)ethyl)piperidinyl)oxy)-4H-benzo[1,4]oxazin-3-one 6-(4-(1-(2-(5-(7-Chloro-2-methyl)quinolinyloxy)ethyl)piperidinyl)oxy)-4-methyl-4H-benzo[1,4]oxazin-3-one 6-(4-(1-(2-(5-(7-Chloro-2-methyl)quinolinyloxy)ethyl)piperazinyl)methyl)-4H-benzo[1,4]oxazin-3-one
6-(4-(1-(2-(5-(2-Methyl)quinolinyloxy)ethyl)piperidinyl)methyl)-4-(2-propyl)-4H-benzo[1,4]oxazin-3-one
6-(4-(1-(2-(5-(2-Methyl)quinazolinyloxy)ethyl)piperidinyl)methyl)-4H-benzo[1,4]-oxazin-3-one
6-(4-(1-(2-(5-(7-Fluoro-2-methyl)quinolinyloxy)ethyl)piperidinyl)methyl)-4H-benzo[1,4]oxazin-3-one
6-(4-(1-(2-(4-benzofuranyloxy)ethyl)piperidinyl)oxy)-4H-benzo[1,4]oxazin-3-one
6-(4-(1-(2-(4-benzofuranyloxy)ethyl)piperidinyl)oxy)-4-methyl-4H-benzo[1,4]oxazin-3-one
6-(4-(1-(2-(1-isoquinolinyloxy)ethyl)piperidinyl)oxy)-4-methyl-4H-benzo[1,4]oxazin-3-one
6-(4-(1-(2-(5-(8-chloro-2-methyl)quinolinyloxy)ethyl)piperidinyl)oxy)-4-methyl-4H-benzo[1,4]oxazin-3-one
6-(4-(1-(2-(1-isoquinolinyloxy)ethyl)piperidinyl)methyl)-4H-benzo[1,4]oxazin-3-one
6-(4-(1-(2-(4-benzofuranyloxy)ethyl)piperazinyl)methyl)-4H-benzo[1,4]oxazin-3-one
6-(4-(1-(2-(1-isoquinolinyloxy)ethyl)piperazinyl)methyl)-4H-benzo[1,4]oxazin-3-one
6-{1-[2-(6-Fluoro-2-methyl-quinolin-5-yloxy)-ethyl]-piperidin-4-ylmethyl}-4H-benzo[1,4]oxazin-3-one
6-{4-[2-(6-Fluoro-2-methyl-quinolin-5-yloxy)-ethyl]-piperazin-1-ylmethyl}-4H-benzo[1,4]oxazin-3-one
6-{1-[2-(7,8-Difluoro-2-methyl-quinolin-5-yloxy)-ethyl]-piperidin-4-ylmethyl}-4H-benzo[1,4]oxazin-3-one
6-{4-[2-(7,8-Difluoro-2-methyl-quinolin-5-yloxy)-ethyl]-piperazin-1-ylmethyl}4H-benzo[1,4]oxazin-3-one
6-{1-[2-(7-Iodo-2-methyl-quinolin-5-yloxy)-ethyl]-piperidin-4-ylmethyl}4H-benzo[1,4]oxazin-3-one
2-Methyl-5-(2-[4-(3-oxo-3,4-dihydro-2H-benzo[1,4]oxazin-6-ylmethyl)-piperidin-1-yl]-ethoxy)-quinoline-7-carbonitrile
6-(4-(1-(2-(5-(2-Methyl)quinolinyloxy)ethyl)piperazinyl)methyl)-4-ethyl-4H-benzo[1,4]oxazin-3-one
6-(4-(1-(2-(5-(2-Methyl)quinolinyloxy)ethyl)piperazinyl)methyl)-4-(1-propyl)-4H-benzo[1,4]oxazin-3-one
6-(4-(1-(2-(5-(2-Methyl)quinolinyloxy)ethyl)piperazinyl)methyl)-4-(1-butyl)-4H-benzo[1,4]oxazin-3-one
6-(4-(1-(2-(5-(2-Methyl)quinolinyloxy)ethyl)piperazinyl)methyl)-4-(2-methyl-1-propyl)-4H-benzo[1,4]oxazin-3-one
6-(4-(1-(2-(5-(2-Methyl)quinolinyloxy)ethyl)piperazinyl)methyl)-4-benzyl-4H-benzo[1,4]oxazin-3-one
6-(4-(1-(2-(5-(2-Methyl)quinolinyloxy)ethyl)piperazinyl)methyl)-4-phenethyl-4H-benzo[1,4]oxazin-3-one
4-Ethyl-6-{1-[2-(2-methyl-quinolin-5-yloxy)-ethyl]-piperidin-4-ylmethyl}4H-benzo[1,4]oxazin-3-one
7,8-Difluoro-6-(4-(1-(2-(5-(2-methyl)quinolinyloxy)ethyl)piperazinyl)methyl)-4H-benzo[1,4]oxazin-3-one
8-Fluoro-6-(4-(1-(2-(5-(2-methyl)quinolinyloxy)ethyl)piperidinyl)methyl)-4H-benzo[1,4]oxazin-3-one
8-Fluoro-4-methyl-6-(4-(1-(2-(5-(2-methyl)quinolinyloxy)ethyl)piperidinyl)methyl)-4H-benzo[1,4]oxazin-3-one
7-Fluoro-6-(4-(1-(2-(5-(2-methyl)quinolinyloxy)ethyl)piperidinyl)methyl)-4H-benzo[1,4]oxazin-3-one
8-Fluoro-6-(4-(1-(2-(5-(2-Methyl)quinazolinyloxy)ethyl)piperidinyl)methyl)-4H-benzo[1,4]-oxazin-3-one
7-Fluoro-6-(4-(1-(2-(5-(2-Methyl)quinazolinyloxy)ethyl)piperidinyl)methyl)-4H-benzo[1,4]-oxazin-3-one
8-Fluoro-6-(4-(1-(2-(5-(7-Chloro-2-methyl)quinolinyloxy)ethyl)piperidinyl)methyl)-4H-benzo[1,4]oxazin-3-one
7-Fluoro-6-(4-(1-(2-(5-(7-Chloro-2-methyl)quinolinyloxy)ethyl)piperidinyl)methyl)-4H-benzo[1,4]oxazin-3-one and pharmaceutically acceptable salts thereof.

Preferred compounds of this invention are:
4-Methanesulfonyl-6-{(4-[2-(2-methylquinolin-5-yloxy)ethyl]piperazin-1-ylmethyl}-3,4-dihydro-2H-benzo[1,4]oxazine,
6-{4-[2-(7-Fluoro-2-methylquinolin-5-yloxy)ethyl]piperazin-1-ylmethyl}4-methanesulfonyl-3,4-dihydro-2H-benzo[1,4]oxazine
6-{4-[2-(2-Methylquinolin-5-yloxy)ethyl]piperazin-1-ylmethyl}-3,4-dihydro-2H-benzo[1,4]oxazine
6-{4-[2-(2-Methylquinolin-5-yloxy)ethyl]piperazin-1-ylmethyl}-3,4-dihydro-2H-benzo[1,4]oxazin-4-yl)ethanone
[3RS]-3-Methoxy-4-methyl-6-{4-[2-(2-methylquinolin-5-yloxy)ethyl]piperazin-1-ylmethyl}-3,4-dihydro-2H-benzo[1,4]oxazine
6-{1-[2-(2-Methylquinolin-5-yloxy)ethyl]piperidin-4-ylmethyl}-3,4-dihydro-2H-benzo[1,4]oxazine
4-Methanesulfonyl-6-{1-[2-(2-methylquinolin-5-yloxy)ethyl]piperidin-4-ylmethyl}-3,4-dihydro-2H-benzo[1,4]oxazine
7-{1-[2-(2-Methylquinolin-5-yloxy)ethyl]piperidin-4-yloxy}-3,4-dihydro-1H-quinolin-2-one
4-Methanesulfonyl-6-{4-[2-(2-methylquinazolin-5-yloxy)ethyl]piperazin-1-ylmethyl}-3,4-dihydro-2H-benzo[1,4]oxazine
6-{4-[2-(2-Methylquinolin-5-yloxy)ethyl]piperazin-1-ylmethyl}quinoxaline
5-{2-[4-(1H-Indol-7-ylmethyl)piperazin-1-yl]ethoxy}-2-methylquinoline
7-Fluoro-4-methanesulphonyl-6-{1-[2-(2-methylquinolin-5-oxy)ethyl]piperidin-4-ylmethyl}-3,4-dihydro-2H-benzo[1,4]oxazine
6-{1-[2-(2-Methylquinolin-5-oxy)ethyl]piperidin-4-ylidenemethyl}-1,3-dihydroindol-2-one
6-{1-[2-(2-Methylquinolin-5-yloxy)ethyl]piperidin-4-ylmethyl}-1,3-dihydroindol-2-one
8-Fluoro-4-methanesulphonyl-6-{1-[2-(2-methylquinolin-5-oxy)ethyl]piperidin-4-ylmethyl}-3,4-dihydro-2H-benzo[1,4]oxazine
8-Fluoro-4-methanesulphonyl-6-{1-[2-(2-methylquinazolin-5-oxy)ethyl]piperidin-4-ylmethyl}-3,4-dihydro-2H-benzo[1,4]oxazine
7-Fluoro-4-methanesulphonyl-6-{1-[2-(2-methylquinazolin-5-oxy)ethyl]piperidin-4-ylmethyl}-3,4-dihydro-2H-benzo[1,4]oxazine and pharmaceutically acceptable salts thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1–19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

Certain compounds of formula (I) are capable of existing in stereoisomeric forms (e.g. geometric (or "cis-trans") isomers, diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof. The present invention includes within its scope all such isomers, including mixtures.

In a further aspect, this invention provides a process for the preparation of a compound of formula (I) or a pharmaceutically acceptable salt thereof, which process comprises:

(a) the coupling of a compound of formula (II):

(II)

wherein A has the same meaning as formula (I) and L is a leaving group, and a compound of formula (III):

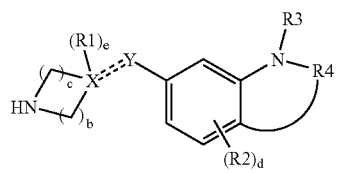
(III)

wherein b, c, d, e, X, Y, R1, R2, R3, R4 and

:::::

have the same meanings as for formula (I);

or (b) for a compound wherein X is nitrogen, the coupling of a compound of formula (IV):

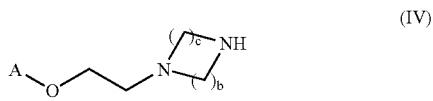
(IV)

wherein A, b and c have the same meanings as for formula (I), and a compound of formula (V):

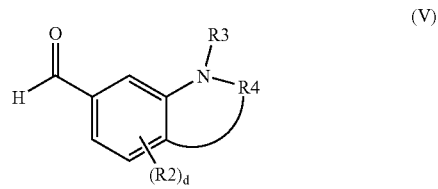
(V)

wherein R2, d, R3 and R4 have the same meanings as for formula (I), and thereafter optionally for process (a) or process (b):
  removing any protecting groups and/or
  converting a compound of formula (I) into another compound of formula (I) and/or
  forming a pharmaceutically acceptable salt.

For process (a), the reaction of compounds of formulae (II) and (III) is preferably carried out in a suitable solvent such as isopropyl alcohol or N,N-dimethylformamide, in the presence of an appropriate base such as N,N-diisopropylethylamine or potassium carbonate. A suitable leaving group L is bromide.

For process (b), the reaction of compounds of formulae (IV) and (V) is preferably carried out in an aprotic solvent such as 1,2-dichloroethane, in the presence of an appropriate reducing agent such as sodium triacetoxyborohydride.

Compounds of formula (I) can be converted into further compounds of formula (I) using standard techniques. For example, and by way of illustration rather than limitation, for compounds of formula (I) wherein

:::::

is a double bond can be converted to compounds of formula (I) in which

:::::

is a single bond by palladium catalysed hydrogenation in a suitable solvent such as ethanol. Other possible conversion reactions include acylation with an appropriate acylating agent such as acetyl chloride, alkylation using an appropriate alkylating reagent such as methyl iodide, and sulfonylation using a sulfonylating agent such as methanesulfonic anhydride.

Compounds of formulae (II), (III), (IV) and (V) are commercially available, may be prepared according to procedures described herein, by known literature methods, or by analogous procedures thereto.

For example, for compounds of the present invention wherein X and Y are both carbon and

:::::

is a double bond, compounds of formula (III) wherein X and Y are both carbon may be prepared by reacting a compound of formula (VI):

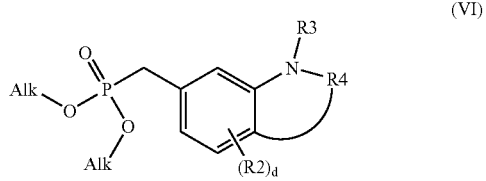
(VI)

wherein "Alk" refers to an alkyl group, with a compound of formula (VII):

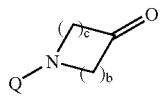

(VII)

wherein Q is a protecting group such as t-butyloxycarbonyl, in the presence of a base such as sodium hydride, in a solvent such as tetrahydrofuran or NN-dimethylformamide.

The protecting group Q may be removed thereafter by any suitable means.

Compounds of formula (VI) may be prepared by treating a compound of formula (VIII):

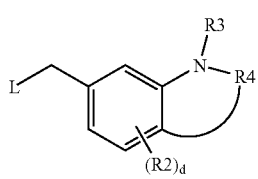

(VIII)

wherein L is a leaving group such as bromide, with a trialkyl phosphite such as triethyl phosphite or trimethyl phosphite, in the absence of solvent or in the presence of a solvent such as toluene.

For compounds of the present invention wherein X is carbon, Y is oxygen and

===== is a single bond, compounds of formula (III) may be prepared by performing a Mitsunobu reaction.

It will be appreciated by those skilled in the art that it may be necessary to protect certain reactive substituents during some of the above procedures. Standard protection and deprotection techniques, such as those described in Greene T. W. *Protective groups in organic synthesis*, New York, Wiley (1981), can be used. For example, primary amines can be protected as phthalimide, benzyl, t-butyloxycarbonyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art. For example, protecting groups such as t-butyloxycarbonyl may be removed using an acid such as hydrochloric or trifluroroacetic acid in a suitable solvent such as dichloromethane, diethylether, isopropanol or mixtures thereof.

Pharmaceutically acceptable salts may be prepared conventionally by reaction with the appropriate acid or acid derivative.

The affinities of the compounds of this invention for $5\text{-HT}_{1A}$, $5\text{-HT}_{1B}$ and $5\text{-HT}_{1D}$ receptors can be determined by the radioligand binding assay as described in WO 99/07700. All compounds tested according to the radioligand binding assay described above were found to have pKi values >6.0 at $5\text{-HT}_{1A}$, $5\text{-HT}_{1B}$ and $5\text{-HT}_{1D}$ receptors, with many showing a considerably higher affinity (having pKi values in the range 8.0–10.0).

The intrinsic activity of the compounds of this invention can be determined according to the $[^{35}S]GTP\gamma S$ functional assay which is also described in WO 99/07700. It has been found, using the $[^{35}S]GTP\gamma S$ functional assay, that certain compounds of formula (I) appear to be antagonists at $5\text{-HT}_1$ type receptors whilst others appear to be inverse agonists, agonists or partial agonists.

The efficacy of the compounds of this invention to inhibit the re-uptake of serotonin can be measured in a 5-HT uptake assay by measurement of uptake of $[^3H]\text{-5-HT}$ into rat cortical synaptosomes as described in Thomas, D. R.; Nelson, D. R.; and Johnson, A. M. *Psychopharmacology* 93:193–200 (1987). Some of the compounds of the present invention were tested according to this 5-HT uptake assay and were found to have potency at the uptake site of pKi >6.0.

Concomitant blockade of $5\text{-HT}_{1A}$, $5\text{-HT}_{1B}$ and $5\text{-HT}_{1D}$ autoreceptors or alternatively blockade of $5\text{-HT}_{1A}$, $5\text{-HT}_{1B}$ and $5\text{-HT}_{1D}$ autoreceptors, in addition to the blockade of serotonin reuptake transporter, has been found to elevate synaptic 5-HT and increase serotonergic transmission, and acutely mimic the effects of chronic treatment with SSRIs. This is expected to result in advantages of increased efficacy, faster onset and a favourable side-effect profile in the clinic.

Compounds of the invention and their pharmaceutically acceptable salts are of use in the treatment of certain CNS disorders such as depression (both bipolar and unipolar), single or recurrent major depressive episodes with or without psychotic features, catatonic features, melancholic features, atypical features or postpartum onset, seasonal affective disorder and dysthymia, anxiety disorders, including generalised anxiety, schizophrenia, panic disorder, agoraphobia, social phobia, obsessive compulsive disorder and post-traumatic stress disorder; pain (particularly neuropathic pain); memory disorders, including dementia, amnesic disorders and age-associated memory impairment; disorders of eating behaviours, including anorexia nervosa and bulimia nervosa, sexual dysfunction, sleep disorders (including disturbances of circadian rhythm, dyssomnia, insomnia, sleep apnea and narcolepsy), withdrawal from abuse of drugs such as of cocaine, ethanol, nicotine, benzodiazepines, alcohol, caffeine, phencyclidine (phencyclidine-like compounds), opiates (e.g. cannabis, heroin, morphine), sedative ipnotic, amphetamine or amphetamine-related drugs (e.g. dextroamphetamine, methylamphetamine) or a combination thereof, motor disorders such as Parkinson's disease, dementia in Parkinson's disease, neuroleptic-induced Parkinsonism and tardive dyskinesias, as well as other psychiatric disorders. Depressive disorders which may be treated or prevented by the compounds of formula (I) and their pharmaceutically acceptable salts may also result from a general medical condition including, but not limited to, myocardial infarction, diabetes, miscarriage or abortion, etc. Compounds of formula (I) may also have utility in the treatment of certain gastrointestinal disorders such as irritable bowel syndrome.

It is to be understood that "treatment" as used herein includes prophylaxis as well as alleviation of established symptoms.

Thus the invention also provides a compound of formula (I) or a pharmaceutically acceptable salt thereof, for use as a therapeutic substance, in particular in the treatment of the above disorders. In particular the invention provides a compound of formula (I) or a pharmaceutically acceptable salt thereof for use as a therapeutic substance in the treatment of a CNS disorder, particularly depression or anxiety.

Compounds of the invention may be administered in combination with other active substances such as 5HT3 antagonists, serotonin agonists, NK-1 antagonists, selective serotonin reuptake inhibitors (SSRI), noradrenaline re-uptake inhibitors (SNRI), tricyclic antidepressants and/or dopaminergic antidepressants.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

It will be appreciated that the compounds of the combination or composition may be administered simultaneously (either in the same or different pharmaceutical formulations), separately or sequentially.

The invention further provides a method of treatment of the above disorders, particularly a CNS disorder such as depression or anxiety, in mammals including humans, which comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment of the above disorders, particularly a CNS disorder such as depression or anxiety.

In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose);, fillers (e.g. lactose, microcrystalline cellulose or calcium hydrogen phosphate);, tabletting lubricants lubricants (e.g. magnesium stearate, talc or silica);, disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salt thereof and a sterile vehicle. Formulations for injection may be presented in unit dosage form e.g. in ampoules or in multi-dose, utilising a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three times a day. Such therapy may extend for a number of weeks or months.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

DESCRIPTION 1

4-Methanesulfonyl-6-methyl-3,4-dihydro-2H-benzo[1,4]oxazine (D1)

6-Methyl-3,4-dihydro-2H-benzo[1,4]oxazine (1.49 g, 10 mmol) was dissolved in dichloromethane (50 mL) and treated with triethylamine (1.14 g, 11 mmol) followed by the dropwise addition of methanesulfonyl chloride (1.26 g, 11 mmol). The mixture was stirred at ambient temperature for 18 h then evaporated to dryness under reduced pressure. The residue was partitioned between ethyl acetate and saturated aqueous $NaHCO_3$. The phases were separated and the organic phase washed with water, saturated brine, dried ($MgSO_4$) and evaporated to dryness under reduced pressure to give the title compound (2.09 g, 93%) as a brown solid.

$^1$H NMR ($CDCl_3$) δ: 2.29 (3H, s), 2.95 (3H, s), 3.88 (2H, t), 4.24 (2H, t), 6.81 (1H, d), 6.86 and 6.88 (1H, dd), 7.50 (1H, d).

DESCRIPTION 2

6-Bromomethyl-4-methanesulfonyl-3,4-dihydro-2H-benzo[1,4]oxazine (D2)

4-Methanesulfonyl-6-methyl-3,4-dihydro-2H-benzo[1,4]oxazine (2.0 g, 8.8 mmol) and N-bromosuccinimide (1.88 g, 10.6 mmol) were dissolved in carbon tetrachloride (100 mL) and the mixture heated at reflux under a 250 W tungsten lamp. After 2 h the mixture was cooled to ambient temperature and filtered through Kieselguhr. The combined filtrate and washings were evaporated to dryness under reduced pressure to give the title compound (2.66 g, 100%) as a brown oil.

DESCRIPTION 3 tert-Butyl 4-(4-methanesulfonyl-3,4-dihydro-2H-benzo[1,4]oxazin-6-ylmethyl)piperazine-1-carboxylate (D3)

6-Bromomethyl-4-methanesulfonyl-3,4-dihydro-2H-benzo[1,4]oxazine (2.6 g, 8.5 mmol) and tert-butyl piperazine-1-carboxylate (1.58 g, 8.5 mmol) were treated with propan-2-ol (100 mL) followed by N,N-diisopropylethylamine (10.96 g, 85 mmol) and the resulting mixture heated at reflux for 72 h then evaporated to dryness under reduced pressure. The residue was partitioned between ethyl acetate and saturated $NaHCO_3$ aq. and the phases separated. The organic phase was washed with water, saturated brine, dried ($MgSO_4$) and evaporated to dryness under reduced pressure. Chromatography on $SiO_2$, eluting with ethyl acetate in 60°–80° petroleum ether, gave the title compound (2.5 g, 71%) as a brown foam.

Mass spectrum ($APCl^+$): Found 412 ($MH^+$). $C_{19}H_{29}N_3O_5S$ requires 411.

$^1$H NMR ($CDCl_3$) δ: 1.45 (9H, s), 2.36–2.38 (4H, m), 2.96 (3H, s), 3.40–3.44 (6H, m), 3.88–3.90 (2H, m), 4.26–4.28 (2H, m), 6.87 (1H, d), 7.02 and 7.04 (1H, dd), 7.61 (1H, d).

DESCRIPTION 4

4-Methanesulfonyl-6-(piperazin-1-ylmethyl)-3,4-dihydro-2H-benzo[1,4]oxazine (D4)

tert-Butyl 4-(4-methanesulfonyl-3,4-dihydro-2H-benzo[1,4]oxazin-6-ylmethyl)piperazine-1-carboxylate (2.5 g, 6.1 mmol) was dissolved in dichloromethane (50 mL) and treated with trifluoroacetic acid (182 mmol). The resulting mixture was stirred at ambient temperature for 3 h then evaporated to dryness under reduced pressure. The residue was extracted with hot ethanol and the combined extracts evaporated to dryness under reduced pressure. Chromatography on $SiO_2$, eluting with 0.880 ammonia/methanol/dichloromethane (1:9:90), gave the title compound (1.2 g, 63%) as an off-white solid.

Mass spectrum ($APCl^+$): Found 312 ($MH^+$). $C_{14}H_{21}N_3O_3S$ requires 311.

$^1$H NMR ($CDCl_3$) δ: 2.29 (4H, m), 2.72 (4H, t), 3.09 (3H, s), 3.35 (2H, s), 3.79 (2H, t), 4.25 (2H, t), 6.86 (1H, d), 6.7 (1H, dd), 7.52 (1H, d).

DESCRIPTION 5 tert-Butyl 4-(2-oxo-1,2,3,4-tetrahydroquinolin-7-yloxy)piperidine-1-carboxylate (D5)

Triphenylphosphine (0.577 g, 2.2 mmol) was dissolved in dry tetrahydrofuran (20 mL) under argon and the solution cooled to 0–5° C. Diisopropyl azodicarboxylate (0.404 g, 2 mmol) was added dropwise and the mixture stirred at 0–5° C. for 20 min. before addition of 7-hydroxy-3,4-dihydro-1H-quinolin-2-one (0.326 g, 2 mmol) and 4-hydroxypiperidine-1-carboxylic acid tert-butyl ester (0.402 g, 2 mmol). The resulting mixture was stirred at ambient temperature for 18 h then evaporated to dryness under reduced pressure.

Chromatography on SiO$_2$, eluting with a gradient of ethyl acetate in 60–80° C. petroleum ether, gave the title compound (0.2 g, 29%) as a white solid.

Mass Spectrum (APCl$^+$): Found 247.2 (MH$^+$). C$_{19}$H$_{26}$N$_2$O$_4$ requires 346.4.

$^1$H NMR (CDCl$_3$) δ: 1.46 (9H, s), 1.70–1.75 (4H, m), 1.83–1.89 (4H, m), 2.62 (2H, t), 2.90 (2H, t), 4.41–4.43 (1H, m), 6.36 (1H, d), 6.53 (1H, dd), 6.81 (1H, d), 8.23 (1H, exchangeable, br).

DESCRIPTION 6

7-(Piperidin-4-yloxy)-3,4-dihydro-1H-quinolin-2-one (D6)

tert-Butyl 4-(2-oxo-1,2,3,4-tetrahydroquinolin-7-yloxy)piperidine-1-carboxylate (0.2 g, 0.58 mmol) was dissolved in dichloromethane (20 mL) and treated with trifluoroacetic acid (1.3 mL). The resulting mixture was stirred at ambient temperature until all the starting material had been consumed, at which time the volatiles were removed by evaporation to dryness under reduced pressure. The residue was neutralized by addition of excess saturated NaHCO$_3$ aq. and the mixture evaporated to dryness under reduced pressure.

Chromatography on SiO$_2$, eluting with a gradient of 10% 0.880 ammonia/methanol in dichloromethane, gave the title compound (0.64 g, 45%) as a white solid.

Mass Spectrum (APCl$^+$): Found 247.2 (MH$^+$). C$_{19}$H$_{26}$N$_2$O$_4$ requires 246.3.

$^1$H NMR (CDCl$_3$) δ: 1.39–1.43 (2H, m), 1.74–1.78 (2H, m), 2.31 (2H, t), 2.44–2.50 (2H, m), 2.63 (2H, t), 2.81–2.85 (2H, m), 4.13–4.19 (1H, m), 6.25 (1H, d), 6.34 (1H, dd), 6.82 (1H, d).

DESCRIPTION 7

5-Fluoro-2-methyl-3,4-dihydroquinazoline (D7)

A solution of 2-amino-6-fluorobenzylamine (1.1 g, 7.86 mmol) and triethylorthoacetate (1.58 mL, 8.64 mmol) in ethanol (30 mL) was heated at 80° C. for 14 h. The reaction mixture was allowed to cool to room temperature and evaporated in vacuo. The yellow oil was triturated with diethyl ether to give the title compound as white solid (0.74 g, 57%). Mass spectrum (API$^+$): Found 165 (MH$^+$). C$_9$H$_9$N$_2$F requires 164.

$^1$H NMR (CDCl$_3$) δ: 2.02 (3H, s), 4.67 (2H, s), 6.34–6.71 (2H, m), 7.03–7.12 (1H, m).

DESCRIPTION 8

5-Fluoro-2-methylquinazoline (D8)

To a solution of 5-fluoro-2-methyl-3,4-dihydroquinazoline (0.74 g, 4.51 mmol) in chloroform (100 mL) at room temperature was added manganese (IV) oxide (4.0 g, 46.0 mmol) and the reaction mixture stirred at room temperature for 20 h. The reaction mixture was filtered through a plug of celite, washing with dichloromethane. The filtrate was evaporated in vacuo to give the title compound as a yellow solid (0.715 g, 98%).

Mass spectrum (API$^+$): Found 163 (MH$^+$). C$_9$H$_7$N$_2$F requires 162.

$^1$H NMR (CDCl$_3$) δ: 2.92 (3H, s), 7.19–7.27 (1H, m), 7.77–7.83 (2H, m), 9.60 (1H, s).

DESCRIPTION 9

2-(2-Methylquinazolin-5-yloxy)ethanol (D9)

To a solution of ethylene glycol (3.05 mL, 55.6 mmol) in N,N-dimethylformamide (50 mL) at room temperature was added sodium hydride (60% dispersion in oil, 0.30 g, 7.50 mmol) portion-wise. The reaction mixture was allowed to stir at room temperature for 30 minutes. A solution of 5-fluoro-2-methylquinazoline (2.22 g, 55.6 mmol) in N,N-dimethylformamide (5 mL) was added and the reaction mixture heated at 85° C. for 14 h. The mixture was allowed to cool to room temperature, quenched by the addition of water and concentrated in vacuo. Chromatography of the residue on SiO$_2$ eluting with 40% ethyl acetate in dichloromethane to ethyl acetate gave the title compound as a yellow solid (0.39 g, 10%).

Mass spectrum (API$^+$): Found 205 (MH$^+$) C$_{11}$H$_{12}$N$_2$O$_2$ requires 204.

$^1$H NMR (CDCl$_3$) δ: 2.87 (3H, s), 4.13–4.16 (2H, m), 4.31–4.33 (2H, m), 6.88 (1H, d, J=8 Hz), 7.50 (1H, d, J=9 Hz), 7.72–7.76 (1H, m), 9.64 (1H, s).

DESCRIPTION 10

5-(2-(Methanesulfonyloxy)ethoxy)-2-methylquinazoline (D10)

To a solution of 2-(2-methylquinazolin-5-yloxy)ethanol (0.330 g, 1.62 mmol) in dichloromethane (20 mL) and triethylamine (0.34 mL, 2.43 mmol) was added methane sulfonyl chloride (0.14 mL, 1.78 mmol) dropwise. The reaction mixture was allowed to stir at room temperature for 2 h. The reaction mixture was diluted with further dichloromethane and partitioned with saturated NaHCO$_3$ aq. The organic phase was washed with brine, dried (MgSO$_4$) and evaporated in vacuo to give the title compound as a cream solid (0.452 g, 99%).

Mass spectrum (ES$^+$): Found 283 (MH$^+$) C$_{12}$H$_{14}$N$_2$O$_4$S requires 282.

$^1$H NMR (CDCl$_3$) δ: 2.89 (3H, s), 3.10 (3H, s), 4.46–4.48 (2H, m), 4.71–4.73 (2H, m), 6.86 (1H, d, J=8 Hz), 7.55 (1H, d, J=9 Hz), 7.74–7.78 (1H, m), 9.69 (1H, s).

DESCRIPTION 11 tert-Butyl 4-[2-(2-methylquinolin-5-yloxy)ethyl]piperazine-1-carboxylate (D11)

tert-Butyl piperazine-1-carboxylate (1.4 g, 7.52 mmol) was added to a mixture of 5-(2-bromoethoxy)-2-methylquinoline (2 g, 7.52 mmol) and potassium carbonate (4.16 g, 30.1 mmol) in N,N-dimethylformamide (20 mL). The reactants were heated at 70° C. for 16 h under an atmosphere of argon. The reaction mixture was poured into water (200 mL) and extracted into ethyl acetate (3×200 mL). The organic layers were combined, dried (Na$_2$SO$_4$) and concentrated in vacuo. The residue was purified by column chromatography, eluting with 30% ethyl acetate in hexane affording the title compound as a tan solid (1.04 g, 37%).

Mass spectrum (API$^+$): Found 372.3 (MH$^+$). C$_{21}$H$_{29}$N$_3$O$_3$ requires 371.

$^1$H NMR (CDCl$_3$) δ: 1.46 (9H, s), 2.59 (4H, t), 2.73 (3H, s), 2.96 (2H, t), 3.46 (4H, t), 4.29 (2H, t), 6.80 (1H, dd), 7.26 (1H, d), 7.58 (2H, m), 8.43 (1H, d).

DESCRIPTION 12

2-Methyl-5-(2-piperazin-1-ylethoxy)quinoline (D12)

tert-Butyl 4-[2-(2-methylquinolin-5-yloxy)ethyl]piperazine-1-carboxylate (1.04 g, 2.8 mmol) was dissolved in ethanol (60 mL) and treated with 1 M hydrochloric acid in diethyl ether (16 mL, 16 mmol) and stirred at 40° C. for 17 h. The reaction mixture was filtered and the white solid was collected and dried in vacuo. The hydrochloride salt precipitate was dissolved in water (25 mL) and potassium carbonate was added until the pH reached 10. The aqueous layer was washed with 5% methanol in dichloromethane (4×100 mL) then 10% methanol in dichloromethane (4×100 mL). The organic layers were combined, dried ($Na_2SO_4$) and concentrated in vacuo, affording the title compound as a brown oil (0.69 g, 91%).

Mass spectrum ($API^+$): Found 272 ($MH^+$). $C_{16}H_{21}N_3O$ requires 271.

$^1H$ NMR ($CDCl_3$) δ: 2.62 (4H, m), 2.73 (3H, s), 2.92 (6H, m), 3.47 (1H, s), 4.29 (1H, d), 6.80 (1H, dd), 7.50 (1H, d), 7.58 (2H, m), 8.45 (1H, d).

DESCRIPTION 13

5-(2-Bromoethoxy)quinoline (D13)

A mixture of 5-hydroxyquinoline (0.3 g, 2.1 mmol), 1,2-dibromoethane (3.9 g, 21 mmol) and potassium carbonate (1.5 g, 11 mmol) in methyl ethyl ketone (15 mL) was allowed to stir at 85° C. for 24 h. The mixture was evaporated in vacuo and the residue was partitioned between ether (200 mL) and water (200 mL). The organic layer was dried over sodium sulfate and evaporated in vacuo to give the title compound (0.53 g).

$^1H$ NMR ($CDCl_3$) δ: 3.80 (2H, m), 4.49 (2H, m), 6.86 (1H, d, J=8 Hz), 7.41 (1H, dd, J=8, 4 Hz), 7.61 (1H, t, J=8 Hz), 7.73 (1H, d, J=8 Hz), 8.64 (1H, d, J=8 Hz), 8.91 (1H, m).

DESCRIPTION 14

5-Hydroxy-2-methylquinoline (D14)

A mixture of 2-methyl-5,6,7,8-tetrahydroquinolin-5-one [E. Reimann, J. Freisinger, *Arch. Pharm.* (*Weinheim*), 318, 871 (1985)] (0.57 g, 3.5 mmol) and 48% aqueous HBr (3.5 mL) was warmed to 60° C. and treated dropwise with bromine (0.19 mL, 0.59 g, 3.6 mmol), with vigorous stirring. The resulting mixture was stirred at 60° C. for 1 h, then evaporated in vacuo. The residue was treated with isopropanol with stirring, then the mixture was evaporated in vacuo to give a waxy solid, which was triturated with 1:1 isopropanol-ether to give a beige powder (0.9 g). A mixture of this material, lithium carbonate (0.48 g, 6.7 mmol), lithium bromide (0.28 g, 3.2 mmol) and N,N-dimethylformamide (10 mL) was heated at 150° C. under argon with stirring for 2 h. The mixture was cooled then evaporated in vacuo. Chromatography of the residue on silica with 0–100% ethyl acetate-hexane gradient elution gave the title compound (0.28 g, 49%) as a solid.

Mass spectrum ($API^+$): Found 160 ($MH^+$). $C_{10}H_9NO$ requires 159.

DESCRIPTION 15

5-(2-Bromoethoxy)-2-methylquinoline (D15)

The title compound was prepared from 5-hydroxy-2-methylquinoline and 1,2-dibromoethane using a similar procedure to Description 13, in 91% yield.

Mass spectrum ($API^+$): Found 266 ($MH^+$). $C_{12}H_{12}{}^{79}BrNO$ requires 265.

DESCRIPTION 16

7-Fluoro-5-hydroxy-2-methylquinoline hydrobromide (D16)

Crotonaldehyde (28 mL, 0.33 mol) was added dropwise to a refluxing solution of 3,5-difluoroaniline (10.75 g, 0.083 mol) in 5 N hydrochloric acid (450 mL) and reflux was continued for a further 0.5 h. Reaction mixture was cooled, diluted with water (200 mL) and washed with ether (200 mL). The aqueous layer was basified (pH 14) with 50% NaOH (aq) and extracted into dichloromethane (3×200 mL). The combined organic phases were dried ($Na_2SO_4$) and evaporated in vacuo to give a dark oil which was purified by chromatography on silica gel (~100 g) with 50–100% ethyl acetate in hexane gradient elution to give 5,7-difluoro-2-methylquinoline as a brown solid (6.57 g, 44%). A mixture of 5,7-difluoro-2-methylquinoline (1.0 g, 5.6 mmol) and sodium methoxide (1.62 g, 30 mmol) in methanol (50 mL), was stirred at reflux for 18 h, cooled, and most of the methanol removed in vacuo. The residue was partitioned between ethyl acetate (100 mL), and water (100 mL). The organic phase was dried ($Na_2SO_4$) and evaporated in vacuo to give a brown oil which was purified by chromatography on silica gel (~60 g) with 20–30% ethyl acetate hexane gradient elution to give a yellow solid (0.57 g) which was suspended in 48% HBr (aq) (5 mL) and heated at reflux for 18 h. Reaction mixture was cooled and evaporated in vacuo to give the title compound as a brown solid (0.67 g, 46%).

Mass spectrum ($API^+$): Found 178 ($MH^+$). $C_{10}H_8FNO$ requires 177.

DESCRIPTION 17

5-(2-Bromoethoxy)-7-fluoro-2-methylquinoline (D17)

The title compound was prepared from 7-fluoro-5-hydroxy-2-methylquinoline hydrobromide and 1,2-dibromoethane using a similar procedure to Description 13, in 91% yield.

DESCRIPTION 18

2-Nitro-4-(piperidin-4-ylmethyl)phenol (D18)

Concentrated nitric acid in acetic acid (8 mL 70% $HNO_3$ aq in 16 mL acetic acid) was added slowly to a stirred solution of 4-(piperidin-4-ylmethyl)phenol (Guzikowski et al, J. Med Chem., 2000, 43, 984–994) (100 mmol) in acetic acid (300 mL) and the resultant slurry stirred at 80° C. for 1 h. The reaction mixture was then filtered and evaporated in vacuo to give the title compound as a brown solid.

DESCRIPTION 19 tert-Butyl 4-(4-hydroxy-3-nitrobenzyl)piperidine-1-carboxylate (D19)

2-Nitro-4-(piperidin-4-ylmethyl)phenol (0.1 mol) was dissolved in water (170 mL) and tetrahydrofuran (170 mL) and treated with triethylamine (14.6 g, 0.14 mol). A solution of di-tert-butyl dicarbonate (16.3 g, 0.12 mol) in tetrahydrofuran (100 mL) was added slowly under argon. The resultant mixture was stirred at room temperature for 18 h. The reaction mixture was partitioned between ethyl acetate and water and the aqueous layer washed with ethyl acetate and the combined extracts dried over $Na_2SO_4$ and evaporated in vacuo, to afford the title compound as a dark oil (40.4 g, 100%).

DESCRIPTION 20

4-(4-Hydroxybenzoyl)piperidine (D20)

A solution of 4-(4-methoxybenzoyl)piperidine hydrochloride (3.0 g, 11.7 mmol), in 48% HBr (aq) (16 mL), and acetic acid (16 mL) was heated at reflux for 48 h. The reaction mixture was evaporated to dryness in vacuo to give an off-white solid which was suspended in saturated $NaHCO_3$ (aq). The resulting precipitate was collected by filtration, washed with water, and dried to give the title compound (1.76 g, 73%) as an off-white solid.

Mass spectrum ($API^+$): Found 206 ($MH^+$). $C_{12}H_{15}NO_2$ requires 205.

DESCRIPTION 21

1-(tert-Butyloxycarbonyl)-4-(4-hydroxy-3-nitrobenzoyl)piperidine (D21)

A solution of 4-(4-hydroxybenzoyl)piperidine (1.52 g, 7.4 mmol) in acetic acid (20 mL) was treated with conc. $HNO_3$ (0.54 mL) in acetic acid (2 mL), and the resulting mixture was stirred at 100° C. for 2 h. Reaction mixture was cooled and evaporated in vacuo to give an orange/brown solid (2.0 g), which was dissolved in a mixture of THF (15 mL), water (4 mL), and triethylamine (1.2 mL), and treated with di-tert-butyldicarbonate (1.62 g, 7.4 mmol). The mixture was stirred at room temperature for 2 h, then evaporated in vacuo, and the residue partitioned between ethyl acetate (100 mL) and water (100 mL). The organic layer was separated and washed twice more with water (2×50 mL), then dried ($Na_2SO_4$) and evaporated in vacuo to give a brown oil (2.4 g) which was purified by chromatography on silica gel (20 g) eluting with 50–100% EtOAc in hexane to give the title compound (1.86, 72%) as a yellow oil.

$^1$H NMR ($CDCl_3$) δ: 1.47 (9H, s), 1.66–1.89 (4H, m), 2.95 (2H, m), 3.37 (1H, m), 4.18 (2H, m), 7.27 (1H, d, J=9 Hz), 8.20 (1H, dd, J=9, 2 Hz), 8.71 (1H, d, J=2 Hz), 10.92 (1H, br s).

DESCRIPTION 22

Methyl 4-(1-(tert-butyloxycarbonyl)piperidin-4-ylcarbonyl)-2-nitrophenoxyacetate (D22)

A mixture of 1-(tert-butoxycarbonyl)-4-(4-hydroxy-3-nitrobenzoyl)piperidine (1.50 g, 4.3 mmol), potassium carbonate (0.77 g, 5.6 mmol), and methyl bromoacetate (0.66 g, 4.3 mmol) in acetone (20 mL) was stirred at reflux for 18 h. The reaction mixture was cooled and evaporated in vacuo, and the residue partitioned between water (20 mL) and dichloromethane (20 mL). The organic layer was separated and washed with 1N NaOH (aq) (20 mL), water (20 mL), and brine (10 mL), dried ($Na_2SO_4$) and evaporated in vacuo to give crude product which was purified by chromatography on silica gel (~20 g) eluting with 10–100% EtOAc in hexane to give the title compound (0.85 g, 47%) as a yellow oil. $^1$H NMR ($CDCl_3$) δ: 1.47 (9H, s), 1.62–1.89 (4H, m), 2.91 (2H, m), 3.35 (1H, m), 3.82 (3H, s), 4.17 (2H, m), 4.88 (2H, s), 7.04 (1H, d, J=9 Hz), 8.13 (1H, dd, J=9, 2 Hz), 8.44 (1H, d, J=2 Hz).

DESCRIPTION 23

Methyl 4-(1-(tert-butyloxycarbonyl)piperidin-4-ylmethyl)-2-nitrophenoxyacetate (D23)

The title compound was prepared from tert-butyl 4-(4-hydroxy-3-nitrobenzyl)piperidine-1-carboxylate in a similar manner to Description 22.

$^1$H NMR ($CDCl_3$) δ: 1.45 (9H, s), 1.59 (5H, m), 2.54 (2H, m), 2.64 (2H, m), 3.80 (3H, s), 4.08 (2H, m), 4.76 (2H, s), 6.92 (1H, d, J=9 Hz), 7.28 (1H, dd, J=9, 2 Hz), 7.65 (1H, d, J=2 Hz).

DESCRIPTION 24

4-Hydroxy-3-nitrophenyl benzoate (D24)

To a stirred solution of 4-hydroxyphenyl benzoate (10 g, 47 mmol) in acetic acid (250 mL) was added, dropwise with external ice-bath cooling, nitric acid (d=1.42, 2.9 mL) (T=10° C.). The mixture was warmed to 20° C. and stirred for a further 56 h. The solution was evaporated in vacuo and water added to the residue. The resulting yellow solid was collected by filtration, washed with water and dried in vacuo to give the title compound (11.8 g, 97%).

$^1$H NMR ($CDCl_3$) δ: 7.23 (1H, d), 7.53 (3H, m), 7.67 (1H, m), 8.00 (1H, d), 8.17 (2H, m), 10.52 (1H, s).

DESCRIPTION 25

4-(Methoxycarbonylmethoxy)-3-nitrophenyl benzoate (D25)

A mixture of 4-hydroxy-3-nitrophenyl benzoate (48.8 g, 0.19 mol), methyl bromoacetate (28.8 g, 0.19 mol), anhydrous potassium carbonate (33.8 g, 0.24 mol) and acetone (700 mL) was heated at reflux for 24 h. The mixture was evaporated in vacuo and the residue partitioned between aqueous NaOH (1 M, 1 L) and dichloromethane (3×200 mL). The combined organic extracts were washed with aqueous NaOH (1 M, 500 mL), water (500 mL) and brine (250 mL), then dried ($Na_2SO_4$) and evaporated in vacuo to give a solid. Crystallisation from methanol following decolourisation with charcoal gave the title compound (38 g, 61%) as pale yellow needles.

$^1$H NMR ($CDCl_3$) δ: 3.83 (3H, s), 4.82 (2H, s), 7.08 (1H, d, J=9 Hz), 7.45 (1H, dd, J=9, 2 Hz), 7.56 (2H, m), 7.67 (1H, m), 7.83 (1H, d, J=2 Hz), 8.19 (2H, m).

DESCRIPTION 26

4-(Methoxycarbonylmethoxy)-3-nitrophenol (D26)

To a stirred suspension of 4-(methoxycarbonylmethoxy)-3-nitrophenyl benzoate (26.2 g, 79 mmol) in methanol (600 mL) at 20° C. was added, dropwise over 0.3 h, a solution of sodium methoxide (4.7 g, 87 mmol) in methanol (300 mL). The resulting mixture was stirred at 20° C. for 2 h then at 50° C. for 1 h. The solution was concentrated to 200 mL in vacuo, then poured into water (1 L) and extracted with diethyl ether-hexane (1:5, 500 mL). The aqueous phase was neutralised with 2 M hydrochloric acid, then extracted with dichloromethane (6×300 mL). The combined dichloromethane extracts were dried (Na$_2$SO$_4$) and evaporated in vacuo to give a semi-solid, which was triturated with ether-hexane (1:3, 2×100 mL) to give the title compound (15.3 g, 85%) as a yellow solid.

$^1$H NMR (CDCl$_3$) δ: 2.00 (1H, br s), 3.80 (3H, s), 4.70 (2H, s), 6.95 (1H, d, J=9 Hz), 7.01 (1H, dd, J=9, 2 Hz), 7.33 (1H, d, J=2 Hz).

DESCRIPTION 27

Methyl 4-(1-(tert-butyloxycarbonyl)piperidin-4-yloxy)-2-nitrophenoxyacetate (D27)

To a stirred solution of 4-(methoxycarbonylmethoxy)-3-nitrophenol (6.0 g, 26.8 mmol), 1-(tert-butyloxycarbonyl)-4-hydroxypiperidine (13.8 g, 68.9 mmol) and triphenylphosphine (18.0 g, 68.9 mmol) in tetrahydrofuran (80 mL) at 20° C. under argon was added diisopropyl azodicarboxylate (13.9 g, 68.9 mmol), dropwise over 0.75 h. The resulting solution was stirred at 20° C. for 4 h, then evaporated in vacuo. Chromatography of the residue on silica (400 g) eluting with 5–50% ether in hexane gave the title compound (10.1 g, 93%) as a yellow oil.

$^1$H NMR (CDCl$_3$) δ: 1.48 (9H, s), 1.65–2.00 (4H, m), 3.34 (2H, m), 3.69 (2H, m), 3.81 (3H, s), 4.44 (1H, m), 4.72 (2H, s), 7.02 (1H, d, J=9 Hz), 7.10 (1H, dd, J=9, 2 Hz), 7.43 (1H, d, J=2 Hz).

DESCRIPTION 28

6-(4-(N-(tert-Butyloxycarbonyl)piperidinyl)oxy)-4H-benzo[1,4]oxazin-3-one (D28)

A mixture of methyl 4-(1-(tert-butyloxycarbonyl)piperidin-4-yloxy)-2-nitrophenoxyacetate (10.1 g, 24.6 mmol), 10% palladium on carbon (1.0 g) and methanol (300 mL) was hydrogenated at 20° C. and 1 bar for 4 h. Catalyst was removed by filtration and the filtrate was evaporated in vacuo to give an oily residue, which was dissolved in toluene. The resulting solution was heated at reflux for 2 h then evaporated in vacuo. Chromatography of the residue on silica with 25–100% ethyl acetate in hexane gave the title compound (7.2 g, 84%) as a colourless solid.

$^1$H NMR (CDCl$_3$) δ: 1.49 (9H, s), 1.74 (2H, m), 1.89 (2H, m), 3.02 (2H, m), 3.68 (2H, m), 4.34 (1H, m), 4.55 (2H, s), 6.44 (1H, d, J=2 Hz), 6.53 (1H, dd, J=9, 2 Hz), 6.89 (1H, d, J=9 Hz), 8.82 (1H, br s).

DESCRIPTION 29

6-(4-(N-(tert-Butyloxycarbonyl)piperidinyl)methyl)-4H-benzo[1,4]oxazin-3-one (D29)

The title compound was prepared from methyl 4-(1-(tert-butyloxycarbonyl)piperidin-4-ylmethyl)-2-nitrophenoxyacetate in a similar manner to Description 28.

$^1$H NMR (CDCl$_3$) δ: 1.45 (9H, s), 1.60 (5H, m), 2.46 (2H, m), 2.63 (2H, m), 4.07 (2H, m), 4.60 (2H, s), 6.57 (1H, d, J=2 Hz), 6.74 (1H, dd, J=9, 2 Hz), 6.89 (1H, d, J=9 Hz), 8.29 (1H, br s).

DESCRIPTION 30

6-Formyl-4H-benzo[1,4]oxazin-3-one (D30)

A mixture of 4-hydroxy-3-nitrobenzaldehyde (3.05 g, 18.3 mmol), ethyl bromoacetate (3.20 g, 19.2 mmol), potassium carbonate (2.77 g, 20.1 mmol) and N,N-dimethylformamide (100 mL) was stirred at 20° C. for 40 h. The resulting solution was partitioned between water (300 mL) and ethyl acetate (300 mL), and the organic phase was washed with water (2×200 mL) and brine (100 mL), then dried (MgSO$_4$) and evaporated in vacuo to give a solid (3.85 g). An aliquot of this solid (0.65 g) was dissolved in acetic acid (16 mL) and iron powder (2.85 g, 50.9 mmol) was added. The mixture was heated to 60° C. for 20 h, then the mixture was cooled and filtered through celite. The filtrate was evaporated in vacuo and the residue was partitioned between ethyl acetate (100 mL) and saturated aqueous NaHCO$_3$. The organic phase was dried (Na$_2$SO$_4$) and evaporated in vacuo to give the title compound (0.31 g, 57%).

$^1$H NMR (DMSO-d$_6$) δ: 4.72 (2H, s), 7.14 (1H, d, J=8 Hz), 7.38 (1H, d, J=2 Hz), 7.54 (1H, dd, J=8, 2 Hz), 9.84 (1H, s), 10.98 (1H, br s).

DESCRIPTION 31

6-(4-(tert-Butyloxycarbonyl)piperazin-1-ylmethyl)-4H-benzo[1,4]oxazin-3-one (D31)

A mixture of 6-formyl-4H-benzo[1,4]oxazin-3-one (1.91 g, 10.8 mmol) and 1-(tert-butoxycarbonyl)piperazine (2.0 g, 10.8 mmol) in 1,2-dichloroethane (120 mL), was cooled in an ice-bath, and treated portionwise with sodium triacetoxyborohydride (3.43 g, 16.2 mmol) over 0.3 h, with stirring under argon. The resulting mixture was stirred at room temperature for 4 h, then partitioned between dichloromethane (100 mL) and saturated aqueous sodium bicarbonate. The organic layer was separated, dried (Na$_2$SO$_4$) and evaporated in vacuo to give the title compound (3.52 g, 94%) as a yellow oil.

$^1$H NMR (CDCl$_3$) δ: 1.46 (9H, s), 2.36 (4H, m), 3.42 (6H, m), 4.61 (2H, s), 6.82 (1H, m), 6.90 (2H, m), 8.86 (1H, br s).

DESCRIPTION 32

6-(4-Piperidinyloxy)-4H-benzo[1,4]oxazin-3-one, hydrochloride (D32)

A mixture of 6-(1-(tert-butyloxycarbonyl)piperidin-4-yloxy)-4H-benzo[1,4]oxazin-3-one (3.78 g, 10.9 mmol), ethereal hydrogen chloride (50 mL) and dichloromethane (20 mL) was heated at 40° C. for 2 h, then allowed to stir at 20° C. for 18 h. The resulting colourless solid was collected by filtration to give the title compound (2.72 g, 88%).

$^1$H NMR (CD$_3$OD) δ: 1.95–2.25 (4H, m), 3.24 (2H, m), 3.40 (2H, m), 4.53 (2H, s), 4.60 (1H, m), 6.60 (1H, d, J=2 Hz), 6.65 (1H, dd, J=9, 2 Hz), 6.92 (1H, d, J=9 Hz).

The following compounds were prepared in a similar manner to Description 32.

(a) 6-(4-Piperidinylmethyl)-4H-benzo[1,4]oxazin-3-one, hydrochloride (D32a)

Mass spectrum (API$^+$): Found 247 (MH$^+$). C$_{14}$H$_{18}$N$_2$O$_2$ requires 246.

(b) 6-(4-Piperazinylmethyl)-4H-benzo[1,4]oxazin-3-one, hydrochloride (D32b)

DESCRIPTION 33

6-(1-(2-(2-Methylquinolin-5-yloxy)ethyl)piperidin-4-ylmethyl)-4H-benzo[1,4]oxazin-3-one (D33)

A mixture of 6-(4-piperidinylmethyl)-4H-benzo[1,4]oxazin-3-one hydrochloride (0.10 g, 0.35 mmol), 5-(2-bromoethoxy)-2-methylquinoline (0.11 g, 0.42 mmol), diisopropylethylamine (1 mL) and isopropanol (10 mL) was heated at reflux under argon for 48 h, cooled, then evaporated in vacuo. The residue was partitioned between saturated aqueous NaHCO$_3$ (50 mL) and dichloromethane (3×30 mL) and the combined organic extracts were dried (Na$_2$SO$_4$) and evaporated in vacuo. The resulting oil was purified by chromatography on silica eluting with 50% ethyl acetate-hexane followed by 0–25% methanol-ethyl acetate gradient elution, to give the title compound (0.04 g, 26%) as an oil.

Mass spectrum (API$^+$): Found 432 (MH$^+$). C$_{26}$H$_{29}$N$_3$O$_3$ requires 431.

$^1$H NMR (CDCl$_3$) δ: 1.25–1.38 (2H, m), 1.49 (1H, m), 1.65 (2H, m), 2.14 (2H, m), 2.45 (2H, d, J=7 Hz), 2.72 (3H, s), 2.94 (2H, t, J=6 Hz), 3.05 (2H, m), 4.27 (2H, t, J=6 Hz), 4.58 (2H, s), 6.56 (1H, d, J=2 Hz), 6.73 (1H, dd, J=7, 2 Hz), 6.78 (1H, d, J=8 Hz), 7.86 (1H, d, J=7 Hz), 7.23 (1H, d, J=8 Hz), 7.50–7.64 (2H, m), 8.42 (1H, d, J=8 Hz), 8.75 (1H, br s).

DESCRIPTION 34

6-(4-(2-(2-Methylquinolin-5-yloxy)ethyl)piperazin-1-ylmethyl)-4H-benzo[1,4]oxazin-3-one (D34)

The title compound was prepared in a similar manner to Description 33.

Mass spectrum (API+): Found 433 (MH$^+$). C$_{25}$H$_{28}$N$_4$O$_3$ requires 432.

$^1$H NMR (CDCl$_3$) δ: 2.50 (4H, m), 2.69 (4H, m), 2.73 (3H, m), 2.97 (2H, t, J=6 Hz), 3.54 (2H, s), 4.30 (2H, t, J=6 Hz), 4.61 (2H, s), 6.79 (2H, m), 6.92 (2H, s), 7.24 (1H, d, J=8 Hz), 7.59 (2H, m), 7.87 (1H, br s), 8.43 (1H, d, J=8 Hz).

DESCRIPTION 35

4-Methyl-6-{(4-[2-(2-methylquinolin-6-yloxy)ethyl]piperazin-1-ylmethyl}4H-benzo[1,4]oxazine (D35)

6-{4-[2-(2-Methylquinolin-6-yloxy)ethyl]piperazin-1-ylmethyl}-3,4-dihydro-2H-benzo[1,4]oxazine (0.14 g, 0.32 mmol) in dry tetrahydrofuran (10 ml) was added dropwise to a suspension of sodium hydride (prepared by washing a 60% dispersion in oil (0.013 g, 0.32 mmol) with 60–80° petroleum ether) in dry tetrahydrofuran (10 ml) under argon. After 15 min, iodomethane (0.046 g, 0.32 mmol) was added and the mixture stirred at ambient temperature for 18 h. The reaction mixture was evaporated to dryness under reduced pressure and the residue partitioned between ethyl acetate and water. The phases were separated and the organic phase washed with water, saturated brine, dried (MgSO$_4$) and evaporated to dryness under reduced pressure. Chromatography on SiO$_2$, eluting with a gradient of 10% 0.880 ammonia/methanol in dichloromethane, gave the title compound (0.104 g, 72%) as a white solid.

Mass Spectrum (APCI$^+$): Found 447 (MH$^+$). C$_{26}$H$_{30}$N$_4$O$_3$ requires 446.

$^1$H NMR (CDCl$_3$) δ: 2.51 (4H, br), 2.69 (4H, br), 2.73 (3H, s), 2.97 (2H, t), 3.37 (3H, s), 3.47 (2H, s), 4.29 (2H, t), 4.60 (2H, s), 6.79 (1H, d), 6.90–6.97 (3H, m), 7.24 (1H, d), 7.53–7.61 (2H, m), 8.43 (1H, d).

DESCRIPTION 36

Diethyl (3-nitrobenzyl)phosphonate (D36)

A mixture of 3-nitrobenzyl bromide (17.3 g, 0.08 mol), triethyl phosphite (13.3 g, 0.08 mol) in toluene (200 mL) was stirred at reflux for 24 h. The reaction mixture was cooled and evaporated in vacuo. Chromatography of the residues on SiO$_2$ eluting from 0–100% ethyl acetate in petroleum ether (60–80° C.) gave the title compound (14.8 g, 68%) as a yellow liquid.

Mass spectrum (API$^+$): Found 274 (MH$^+$). C$_{11}$H$_{16}$NO$_5$P requires 273.

$^1$H NMR (CDCl$_3$) δ: 1.28 (6H, m), 3.26 (2H, d, J=22 Hz), 4.11 (4H, m), 7.51 (1H, t, J=8 Hz), 7.67 (1H, m), 8.15 (2H, m).

DESCRIPTION 37 tert-Butyl 4-(3-nitrobenzylidene)piperidine-1-carboxylate (D37)

A mixture of diethyl (3-nitrobenzyl)phosphonate (8.4 g, 0.031 mol) and tert-butyl 4-oxopiperidine-1-carboxylate (6.12 g, 0.031 mol) in dry tetrahydrofuran (120 mL) was treated with a 60% suspension of sodium hydride in oil (1.36 g, 0.034 mmol). The resulting mixture was stirred at room temperature for 4 h, then partitioned between dichloromethane (500 mL) and water (500 mL). The organic extract was dried (Na$_2$SO$_4$) and evaporated in vacuo to give the title compound (9.86 g, 100%) as a solid.

$^1$H NMR (CDCl$_3$) δ: 1.48 (9H, s), 2.38 (2H, m), 2.45 (2H, m), 3.43 (2H, m), 3.53 (2H, m), 6.39 (1H, s), 7.49 (2H, m), 8.06 (2H, m),

DESCRIPTION 38 tert-Butyl (4-fluoro-3-nitrobenzylidene)piperidine-1-carboxylate (D38)

The title compound was prepared in an analogous manner to Description 37.

DESCRIPTION 39

Dimethyl 2-[4-(1-tert-butoxycarbonylpiperidin-4-ylidenemethyl)-2-nitrophenyl]malonate (D39)

Sodium hydride (60% dispersion in oil; 333 mg; 8.4 mmol) was washed with 60–80° C. petroleum ether and suspended in dry dimethylsulphoxide (10 ml) under argon. Dimethyl malonate (1.1 g; 8.4 mmol) was added dropwise and, when the effervescence had subsided, the reaction mixture was heated at 100° C. for 1 h. The resulting solution was cooled to ambient temperature and treated with a solution of tert-butyl (4-fluoro-3-nitrobenzylidene)piperidine-1-carboxyate (1.4 g; 4.2 mmol) in dry dimethylsulphoxide (10 ml). This mixture was stirred at ambient temperature for 18 h then poured into saturated aq. ammonium chloride solution and extracted with ethyl acetate. The combined organic extracts were washed with H$_2$O, saturated brine, dried (MgSO$_4$) and evaporated to dryness under reduced pressure. Chromatography on SiO$_2$, eluting with dichloromethane, gave the title compound (1.65 g; 88%) as a yellow oil.

$^1$H NMR (CDCl$_3$) δ: 1.48 (9H, s), 2.36 (2H, t, J 5), 2.45 (2H, t, J 5), 3.42 (2H, t, J 6), 3.52 (2H, t J 6), 3.81 (6H, s), 5.31 (1H, s), 6.34 (1H, s), 7.45 (2H, s), 7.87 (1H, s).

DESCRIPTION 40

6-(Piperidin-4-ylidenemethyl)-1,3-dihydroindol-2-one (D40)

Dimethyl 2-[4-(1-tert-butoxycarbonylpiperidin-4-ylidenemethyl)-2-nitrophenyl]malonate (1.65 g; 3.7 mmol) was dissolved in ethanol (50 ml), tin powder (1.31 g; 11 g atom)

was added followed by conc. hydrochloric acid (10 ml) and the mixture heated at reflux for 3 h before being left to stand at ambient temperature for 18 h. Evaporated to dryness under reduced pressure, water added to the residue and the insoluble material removed by filtration. The filtrate and washings were combined and evaporated to dryness under reduced pressure and this residue extracted with hot methanol. The insoluble materials were further extracted with hot ethanol, the extracts combined and evaporated to dryness under reduced pressure to give the title compound (680 mg; 81%) as a brown foam.

Mass Spectrum (APCI$^+$): Found 229 (MH$^+$). $C_{14}H_{16}N_2O$ requires 228.

$^1$H NMR (MeOD) δ: 2.36 (2H, t J 6), 2.48 (2H, t J 6), 2.82 (2H, t J 6), 2.92 (2H, t J 6), 3.37 (2H, s, exchangeable), 6.31 (1H, s), 6.73 (1H, s), 6.82 and 6.84 (1H, dd J4 and 7), 7.18 (1H, d J 7).

EXAMPLE 1

4-Methanesulfonyl-6-{4-[2-(2-methylquinolin-5-yloxy)ethyl]piperazin-1-ylmethyl}-3,4-dihydro-2H-benzo[1,4]oxazine (E1)

The title compound was prepared by reaction of 4-methanesulfonyl-6-(piperazin-1-ylmethyl)-3,4-dihydro-2H-benzo[1,4]oxazine (0.145 g, 1 mmol), 5-(2-bromoethoxy)-2-methylquinoline (0.266 g, 1 mmol) and N,N-diisopropylethylamine (1.29 g, 10 mmol) in isopropyl alcohol (8 mL). The mixture was heated at reflux with stirring in a reaction block for 48 h. The reaction mixture was cooled, and the isopropyl alcohol evaporated in vacuo. The residue was partitioned between dichloromethane (5 mL), and water (5 mL). The organic layer was added onto a 10 g pre-packed silica column and eluted with 0–10% methanol in ethyl acetate. Fractions containing desired material were combined and evaporated in vacuo to give the title compound (0.180 g, 36%) as a colourless solid. Mass Spectrum (APCI$^+$): Found 497 (MH$^+$). $C_{28}H_{32}N_4O_4S$ requires 496.

$^1$H NMR (CDCl$_3$) δ: 2.43 (4H, m), 2.60 (4H, m), 2.64 (3H, s), 2.85–2.88 (5H, m), 3.38 (2H, s), 3.78–3.81 (2H, m), 4.16–4.20 (4H, m), 6.70 (1H, dd), 6.79 (1H, d), 6.5 (1H, dd), 7.16 (1H, d), 7.44–7.53 (3H, m), 8.35 (1H, d).

EXAMPLE 2

6-{4-[2-(7-Fluoro-2-methylquinolin-5-yloxy)ethyl]piperazin-1-ylmethyl}-4-methanesulfonyl-3,4-dihydro-2H-benzo[1,4]oxazine (E2)

The title compound (0.101 g, 39%) was prepared from 4-methanesulfonyl-6-(piperazin-1-ylmethyl)-3,4-dihydro-2H-benzo[1,4]oxazine (0.156 g, 0.5 mmol), 2-(5-(7-fluoro-2-methyl)quinolinyl)oxyethyl bromide (0.142 g, 0.5 mmol) and N,N-diisopropylethylamine (0.646 g, 5 mmol) by the method described in Example 1.

Mass Spectrum (APCI$^+$): Found 515 (MH$^+$). $C_{26}H_{31}FN_4O_4S$ requires 514.

$^1$H NMR (CDCl$_3$) δ: 2.50 (4H, m), 2.67 (4H, m), 2.70 (3H, s), 2.93–2.96 (5H, m), 3.46 (2H, s), 3.88 (2H, t), 4.23–4.27 (4H, m), 6.8 (1H, dd), 6.87 (1H, d), 7.03 (1H, dd), 7.18–7.27 (2H, m), 7.62 (1H, d), 8.35 (1H, d).

EXAMPLE 3

6-{4-[2-(2-Methylquinolin-5-yloxy)ethyl]piperazin-1-ylmethyl}-3,4-dihydro-2H-benzo[1,4]oxazine (E3)

6-(4-(2-(2-Methylquinolin-5-yloxy)ethyl)piperazin-1-ylmethyl)-4H-benzo[1,4]oxazin-3-one (0.139 g, 0.32 mmol) was dissolved in dry tetrahydrofuran (10 mL) under argon and treated with a solution of lithium aluminium hydride in tetrahydrofuran (1 M, 0.32 mL, 0.32 mmol) and the reaction stirred at ambient temperature. More lithium aluminium hydride solution (1 M in tetrahydrofuran, 0.32 mL, 0.32 mmol) was added after 18 h and the mixture stirred for 1 h before being quenched with 10% potassium sodium tartrate aq. and extracted with ethyl acetate. The combine organic extracts were washed with water, saturated brine, dried (MgSO$_4$) and evaporated to dryness under reduced pressure. Chromatography on SiO$_2$, eluting with a gradient of 10% 0.880 ammonia/methanol in dichloromethane, gave the title compound (0.073 g, 54%) as a yellow foam.

Mass Spectrum (APCI$^+$): Found 419 (MH$^+$). $C_{25}H_{30}N_4O_2$ requires 418.

$^1$H NMR (CDCl$_3$) δ: 2.49 (4H, br m), 2.67 (4H, br m), 2.72 (3H, s), 2.91–2.97 (2H, m), 3.36–3.41 (4H, m), 4.22–4.36 (4H, m), 6.56–6.79 (3H, m), 7.22–7.26 (2H, m), 7.52 and 7.61 (2H, m), 8.40–8.44 (1H, m).

EXAMPLE 4

6-{4-[2-(2-Methylquinolin-5-yloxy)ethyl]piperazin-1-ylmethyl}-3,4-dihydro-2H-benzo[1,4]oxazin-4-yl)ethanone (E4)

6-{4-[2-(2-Methylquinolin-5-yloxy)ethyl]piperazin-1-ylmethyl}-3,4-dihydro-2H-benzo[1,4]oxazine (0.031 g, 0.07 mmol) was dissolved in dichloromethane (10 mL) and treated with triethylamine (0.0082 g, 0.08 mmol) and acetyl chloride (0.0064 g, 0.08 mmol) and the mixture stirred at ambient temperature for 18 h. The mixture was then evaporated to dryness under reduced pressure and the residue purified by chromatography on SiO$_2$, eluting with a gradient of 10% 0.880 ammonia/methanol in dichloromethane, to give the title compound (0.013 g, 38%) as a yellow foam.

Mass Spectrum (APCI$^+$): Found 461 (MH$^+$). $C_{27}H_{32}N_4O_3$ requires 460.

$^1$H NMR (CDCl$_3$) δ: 2.33 (3H, s), 2.51–2.74 (11H, m), 2.92–2.98 (2H, m), 3.45 (2H, s), 3.94 (2H, br), 4.24–4.29 (4H, m), 6.70–7.27 (5H, m), 7.53–7.61 (2H, m), 8.41–8.44 (1H, m).

EXAMPLE 5

[3RS]-3-Methoxy-4-methyl-6-{4-[2-(2-methylquinolin-5-yloxy)ethyl]piperazin-1-ylmethyl}-3,4-dihydro-2H-benzo[1,4]oxazine The title compound (0.063 g, 76%) was prepared from 4-methyl-6-{4-[2-(2-methylquinolin-5-yloxy)ethyl]piperazin-1-ylmethyl}4H-benzo[1,4]oxazine (0.08 g, 0.2 mmol) as described in Example 3.

Mass Spectrum (APCI$^+$): Found 431 (MH—CH$_3$OH)$^+$. $C_{27}H_{34}N_4O_3$ requires 462.

$^1$H NMR (CDCl$_3$) δ: 2.51 (4H, m), 2.68 (4H, m), 2.72 (3H, s), 2.96 (2H, t), 3.07 (3H, s), 3.42 (5H, br s), 3.93 and 3.96 (1H, dd), 4.28 (2H, t), 4.35 (1H, dd), 4.52 (1H, t), 6.61–6.63 (2H, m), 6.75–6.80 (2H, m), 7.23–7.26 (1H, m), 7.52–7.61 (2H, m), 8.43 (1H, m).

EXAMPLE 6

6-{1-[2-(2-Methylquinolin-5-yloxy)ethyl]piperidin-4-ylmethyl}-3,4-dihydro-2H-benzo[1,4]oxazine (E6)

The title compound (0.228 g, 54%) was prepared by reduction of 6-{1-[2-(2-methylquinolin-5-yloxy)ethyl]piperidin-4-ylmethyl}-4H-benzo[1,4]oxazin-3-one (0.431 g, 1 mmol) with lithium aluminium hydride as described in Example 3.

Mass Spectrum (APCl$^+$): Found 418 (MH$^+$). $C_{26}H_{31}N_3O_2$ requires 417.

$^1$H NMR (CDCl$_3$) δ: 1.25–1.35 (2H, m), 1.45–1.49 (1H, m), 1.65–1.69 (2H, m), 2.10–2.16 (2H, m), 2.38 (2H, d), 2.72 (3H, s), 2.89–2.93 (2H, m), 3.01–3.04 (2H, m), 3.39–3.41 (2H, m), 4.21–4.28 (4H, m), 6.37 (1H, d), 6.43 (1H, dd), 6.68 (1H, d), 6.79 (1H, d), 7.21–7.25 (1H, m), 7.52–7.60 (2H, m), 8.43 (1H, d).

EXAMPLE 7

4-Methanesulfonyl-6-{1-[2-(2-methylquinolin-5-yloxy)ethyl]piperidin-4-ylmethyl}-3,4-dihydro-2H-benzo[1,4]oxazine (E7)

The title compound (0.07 g, 73%) was prepared from 6-{1-[2-(2-methylquinolin-5-yloxy)ethyl]piperidin-4-ylmethyl}-3,4-dihydro-2H-benzo[1,4]oxazine (0.081 g, 0.19 mmol) by the method described in Description 1.

Mass Spectrum (APCI$^+$): Found 496 (MH$^+$). $C_{27}H_{33}N_3O_4S$ requires 495.

$^1$H NMR (CDCl$_3$) δ: 1.26–1.38 (2H, m), 1.49–1.54 (1H, m), 1.64–1.67 (2H, m), 2.12–2.17 (2H, m), 2.48 (2H, d), 2.72 (3H, s), 2.91–2.94 (5H, m), 3.02–3.05 (2H, m), 3.88 (2H, t), 4.23–4.28 (4H, m), 6.78–6.86 (3H, m), 7.24 (1H, d), 7.47–7.60 (3H, m), 8.43 (1H, d).

EXAMPLE 8

7-{1-[2-(2-Methylquinolin-5-yloxy)ethyl]piperidin-4-yloxy}-3,4-dihydro-1H-quinolin-2-one (E8)

7-(Piperidin-4-yloxy)-3,4-dihydro-1H-quinolin-2-one (0.064 g, 0.25 mmol) and 5-(2-bromoethoxy)-2-methylquinoline (0.069 g, 0.25 mmol) were mixed together in propan-2-ol (20 mL), N,N-diisopropylethylamine (0.336 g, 2.6 mmol) added and the mixture heated at reflux for 48 h. The volatiles were removed by evaporation to dryness under reduced pressure and the residue partitioned between ethyl acetate and saturated NaHCO$_3$ aq. The phases were separated, the organic phase washed with water, dried (MgSO$_4$) and evaporated to dryness under reduced pressure. Chromatography on SiO$_2$, eluting with a gradient of ethyl acetate in 60–80° C. petroleum ether, gave the title compound (0.05 g, 45%) as a white solid, after trituration under 60–80° C. petroleum ether.

Mass Spectrum (APCl$^+$): Found 432.1 (MH$^+$). $C_{26}H_{29}N_3O_3$ requires 431.5.

$^1$H NMR (CDCl$_3$) δ: 1.84–1.87 (2H, m), 1.98–2.03 (2H, m), 2.54–2.56 (2H, m), 2.59–2.63 (2H, m), 2.73 (3H, m), 2.87–2.92 (4H, m), 2.98 (2H, t), 4.28–4.32 (3H, m), 6.36 (1H, d), 6.53 (1H, dd), 6.81 (1H, d), 7.03 (1H, d), 7.25 (1H, d), 7.53–7.62 (2H, m), 8.27 (1H, br), 8.44 (1H, d).

EXAMPLE 9

4-Methanesulfonyl-6-{4-[2-(2-methylquinazolin-5-yloxy)ethyl]piperazin-1-ylmethyl}-3,4-dihydro-2H-benzo[1,4]oxazine (E9)

The title compound was prepared from 4-methanesulfonyl-6-(piperazin-1-ylmethyl)-3,4-dihydro-2H-benzo[1,4]oxazine and 5-(2-(methanesulfonyloxy)ethoxy)-2-methylquinazoline following the method of Example 1.

Mass Spectrum (APCl$^+$): Found 498 (MH$^+$). $C_{25}H_{31}N_5O_4S$ requires 497.

$^1$H NMR (CDCl$_3$) δ: 2.50 (4H, m), 2.69 (4H, m), 2.88 (3H, s), 2.97–2.99 (5H, m), 3.46 (2H, s), 3.89 (2H, t), 4.26–4.32 (4H, m), 6.84–6.89 (2H, m), 7.04 (1H, dd), 7.49 (1H, d), 7.61 (1H, d), 7.74 (1H, m), 9.63 (1H, s).

EXAMPLE 10

6-{4-[2-(2-Methylquinolin-5-yloxy)ethyl]piperazin-1-ylmethyl}quinoxaline (E10)

A mixture of 2-methyl-5-(2-piperazin-1-ylethoxy)quinoline (0.054 g, 0.2 mmol) and quinoxaline-6-carboxyaldehyde (0.032 g, 0.2 mmol) in 1,2-dichloroethane (5 mL) was treated with sodium triacetoxyborohydride (64 mg, 0.2 mmol) and stirred at 20° C. under an atmosphere of argon for 24 h. The mixture was then treated with saturated aqueous NaHCO$_3$ (20 mL) and the organic layer separated and purified directly by chromatography on silica (ethyl acetate to 10% methanol/ethyl acetate), to afford the title compound (0.05 g, 61%) as a solid.

Mass spectrum (API$^+$): Found 414 (MH$^+$). $C_{25}H_{27}N_5O$ requires 413.

EXAMPLE 11

5-{2-[4-(1H-Indol-7-ylmethyl)piperazin-1-yl]ethoxy}-2-methylquinoline (E11)

A mixture of 2-methyl-5-(2-piperazin-1-ylethoxy)quinoline (0.04 g, 0.15 mmol) and indole-7-carboxyaldehyde (0.023 g, 0.15 mmol) in 1,2-dichloroethane (2.5 mL) was treated with sodium triacetoxyborohydride (50 mg, 0.24 mmol) and stirred at 20° C. under an atmosphere of argon for 24 h. The mixture was then treated with saturated aqueous NaHCO$_3$ (20 mL) and the organic layer separated and purified directly by chromatography on silica (ethyl acetate to 10% methanol/ethyl acetate), to afford the title compound (0.042 g, 71%) as a solid.

Mass spectrum (API$^+$): Found 401 (MH$^+$). $C_{25}H_{28}N_4$ requires 400.

EXAMPLE 12

7-Fluoro-4-methanesulphonyl-6-{1-[2-(2-methylquinolin-5-oxy)ethyl]piperidin-4-ylmethyl}-3,4-dihydro-2H-benzo[1,4]oxazine (E12)

The title compound was prepared in an analogous manner to Example 7.

Mass Spectrum (APCl$^+$): Found 514 (MH$^+$). $C_{27}H_{32}FN_3O_4S$ requires 513.

$^1$H NMR (CDCl$_3$) δ: 1.34–1.41 (2H, m), 1.53–1.56 (1H, m), 2.13–2.19 (2H, m), 2.52 (2H, d), 2.72 (3H, s), 2.92–2.94 (5H, m), 3.02–3.05 (2H, m), 3.86 (2H, t), 4.23–4.28 (4H, m), 6.61 (1H, d), 6.79 (1H, m), 7.24 (1H, d), 7.44 (1H, d), 7.52–7.60 (2H, m), 8.43 (1H, d).

EXAMPLE 13

6-{-[2-(2-Methylquinolin-5-oxy)ethyl]piperidin-4-ylidenemethyl}-1,3-dihydroindol-2-one (E13)

The title compound was prepared from 6-(piperidin-4-ylidenemethyl)-1,3-dihydroindol-2-one and 5-(2-bromoethoxy)-2-methylquinoline using a similar method to that of Description 11.

Mass Spectrum (APCl$^+$): Found 414 (MH$^+$). $C_{26}H_{27}N_3O_2$ requires 413.

$^1$H NMR (CDCl$_3$) δ: 2.42–2.45, 2.54–2.57, 2.63–2.66 and 2.75–2.78 (each 2H, 4 m), 2.72 (3H, d), 2.98–3.01 (2H, m), 3.50 (2H, brs), 4.30 (2H, t), 6.25 (1H, s), 6.72 (1H, s), 6.78–6.84 (2H, m), 7.14 (1H, d), 7.23 (1H, d), 7.53–7.62 (2H, m), 8.42 (1H, d), 9.44 (1H, s, exchangeable).

EXAMPLE 14

6-{1-[2-(2-Methylquinolin-5-yloxy)ethyl]piperidin-4-ylmethyl}-1,3-dihydroindol-2-one (E14)

6-{1-[2-(Methylquinolin-5-yloxy)ethyl]piperidin-4-ylidenemethyl}-1,3-dihydroindol-2-one (150 mg; 0.36 mmol) was dissolved in a mixture of methanol (20 ml) and tetrahydrofuran (20 ml). Ammonium formate (229 mg; 3.6 mmol) was added, followed by 10% palladium on carbon (150 mg), and the resulting mixture stirred vigorously at ambient temperature for 2 h. The reaction mixture was filtered through Kieselguhr and the filtrate evaporated to dryness under reduced pressure. Chromatography on SiO$_2$, eluting with 10% aq. ammoniacal methanol in dichloromethane (5:95), gave the title compound (150 mg; 100%) as a white foam.

Mass Spectrum (APCl$^+$): Found 416 (MH$^+$). $C_{26}H_{29}N_3O_2$ requires 415.

$^1$H NMR (CDCl$_3$) δ: 1.31–1.38 (2H, m), 1.50–1.54 (1H, m), 1.64–1.67 (2H, m), 2.11–2.17 (2H, m), 2.50 (2H, d), 2.72 (3H, s), 2.93 (2H, t), 3.03–3.06 (2H, m), 3.49 (2H, s), 4.27 (2H, t), 6.67 (1H, s), 6.78 (1H, d), 7.10 (1H, d), 7.22 (1H, d), 7.23 (1H, d), 7.52–7.60 (2H, m), 8.41 (1H, d), 8.82 (1H, brs, exchangeable).

EXAMPLE 15

8-Fluoro-4-methanesulphonyl-6-{1-[2-(2-methylquinolin-5-oxy)ethyl]piperidin-4-ylmethyl}-3,4-dihydro-2H-benzo[1,4]oxazine (E15)

The title compound was prepared in an analogous manner to Example 7.

Mass Spectrum (APCl$^+$): Found 514 (MH$^+$). $C_{27}H_{32}FN_3O_4S$ requires 513.

$^1$H NMR (CD$_3$OD) δ: 1.64–1.70 (2H, m), 1.92–2.02 (3H, m), 2.56 (2H, d J 6), 2.72 (3H, s), 3.05 (3H, s), 3.22–3.24 (2H, m), 3.71–3.75 (4H, m), 3.88 (2H, t J 4), 4.31 (2H, t J 4), 4.61 (2H, t J 4), 6.80 (1H, dd J 11.5 and 2), 7.07 (1H, d J 8), 7.30 (1H, s), 7.46 (1H, d J 9), 7.60 (1H, d J 8), 7.68 (1H, d J 8), 8.70 (1H, d J 8).

EXAMPLE 16

8-Fluoro-4-methanesulphonyl-6-{1-[2-(2-methylquinazolin-5-oxy)ethyl]piperidin-4-ylmethyl}-3,4-dihydro-2H-benzo[1,4]oxazine (E16)

The title compound was prepared in an analogous manner to Example 7.

Mass Spectrum (APCl$^+$): Found 515 (MH$^+$). $C_{26}H_{31}FN_4O_4S$ requires 514.

$^1$H NMR (CDCl$_3$) δ: 1.26–1.38 (2H, m), 1.49–1.53 (1H, m), 1.64–1.67 (2H, m), 2.17–2.22 (2H, m), 2.47 (2H, d J 7), 2.88 (3H, s), 2.96–2.98 (5H, m), 3.05–3.08 (2H, m), 3.92 (2H, t J 5), 4.30–4.33 (4H, m), 6.70 (1H, dd J 11 and 2), 6.85 (1H, d J 8), 7.27 (1H, d J 8), 7.49 (1H, d J 8), 7.7 (1H, t J 8), 9.62 (1H, s).

EXAMPLE 17

7-Fluoro-4-methanesulphonyl-6-{1-[2-(2-methylquinazolin-5-oxy)ethyl]piperidin-4-ylmethyl}-3,4-dihydro-2H-benzo[1,4]oxazine (E17)

The title compound was prepared in an analogous manner to Example 7.

Mass Spectrum (APCl$^+$): Found 515 (MH$^+$). $C_{26}H_{31}FN_4O_4S$ requires 514.

$^1$H NMR (CD$_3$OD) δ: 1.41–1.47 (2H, m), 1.66–1.67 (1H, m), 1.72–1.76 (2H, m), 2.37–2.43 (2H, m), 2.54 (2H, d J 7), 2.81 (3H, s), 2.99 (3H, s), 3.11–3.14 (2H, m), 3.21–3.24 (2H, m), 3.83 (2H, t J 5), 4.27 (2H, J 5), 4.43 (2H, t J 5), 6.63–6.65 (1H, m), 7.11 (1H, d J 8), 7.46–7.49 (2H, m), 7.89 (1H, t J 8), 9.70 (1H, s).

The invention claimed is:

1. A compound of formula (I) or a pharmaceutically acceptable salt thereof:

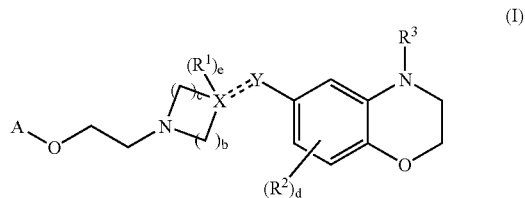

wherein:
A is optionally substituted phenyl, naphthyl, indolyl, quinolinyl, quinazolinyl, indazolyl, isoquinolinyl or benzofuranyl,
b is 1, 2 or 3 and c is 1, 2 or 3, wherein b+c is 2, 3, 4 or 5;
X is carbon, Y is CH,

===== is a double bond and e is 0; or X is carbon, Y is CH$_2$ or oxygen,

===== is a single bond and e is 1; or X is nitrogen, Y is CH$_2$,

===== is a single bond and e is 0;
R$^1$ is hydrogen, cyano, halogen, C$_{1-6}$alkyl, C$_{1-6}$alkoxy, C$_{1-6}$alkoxyC$_{1-6}$alkyl, NHCOCH$_3$ or OCONR$^5$R$^6$, wherein R$^5$ and R$^6$ are independently hydrogen or C$_{1-6}$alkyl;
R$^2$ is halogen, cyano or C$_{1-6}$alkoxy;
d is 0, 1, 2 or 3; and
R$^3$ is hydrogen, C$_{1-6}$alkyl, C$_{1-6}$alkanoyl, fluoroC$_{1-6}$alkanoyl, C$_{1-6}$alkylsulfonyl, fluoroC$_{1-6}$alkylsulfonyl, carbamoyl, C$_{1-6}$alkylcarbamoyl or arylC$_{1-6}$alkyl.

2. A compound as claimed in claim 1, wherein A is quinolinyl or quinazolinyl.

3. A compound as claimed in claim 2, wherein A is 5-(2-methyl)quinolinyl or 5-(2-methyl)quinazolinyl.

4. A compound as claimed in claim 1, wherein $R^2$ is fluoro.

5. A compound as claimed in claim 1, wherein d is 0, 1 or 2.

6. A compound as claimed in claim 1, wherein $R^3$ is hydrogen, $C_{1-6}$alkyl or $C_{1-6}$alkylsulfonyl.

7. A compound which is:

4-methanesulfonyl-6-{4-[2-(2-methylquinolin-5-yloxy)ethyl]piperazin-1-ylmethyl}-3,4-dihydro-2H-benzo[1,4]oxazine;

6-{4-[2-(7-fluoro-2-methylquinolin-5-yloxy)ethyl]piperazin-1-ylmethyl}-4-methanesulfonyl-3,4-dihydro-2H-benzo[1,4]oxazine;

6-{4-[2-(2-methylquinolin-5-yloxy)ethyl]piperazin-1-ylmethyl}-3,4-dihydro-2H-benzo[1,4]oxazine;

6-{4-[2-(2-methylquinolin-5-yloxy)ethyl]piperazin-1-ylmethyl}-3,4-dihydro-2H-benzo[1,4]oxazin-4-yl)ethanone;

[3RS]-3-methoxy-4-methyl-6-{4-[2-(2-methylquinolin-5-yloxy)ethyl]piperazin-1-ylmethyl}-3,4-dihydro-2H-benzo[1,4]oxazine;

6-{1-[2-(2-methylquinolin-5-yloxy)ethyl]piperidin-4-ylmethyl}-3,4-dihydro-2H-benzo[1,4]oxazine;

4-methanesulfonyl-6-{1-[2-(2-methylquinolin-5-yloxy)ethyl]piperidin-4-ylmethyl}-3,4-dihydro-2H-benzo[1,4]oxazine;

4-methanesulfonyl-6-{4-[2-(2-methylquinazolin-5-yloxy)ethyl]piperazin-1-ylmethyl}-3,4-dihydro-2H-benzo[1,4]oxazine;

7-fluoro-4-methanesulphonyl-6-{1-[2-(2-methylquinolin-5-oxy)ethyl]piperidin-4-ylmethyl}-3,4-dihydro-2H-benzo[1,4]oxazine;

8-fluoro-4-methanesulphonyl-6-{1-[2-(2-methylquinolin-5-oxy)ethyl]piperidin-4-ylmethyl}-3,4-dihydro-2H-benzo[1,4]oxazine;

8-fluoro-4-methanesulphonyl-6-{1-[2-(2-methylquinazolin-5-oxy)ethyl]piperidin-4-ylmethyl}-3,4-dihydro-2H-benzo[1,4]oxazine;

7-fluoro-4-methanesulphonyl-6-{1-[2-(2-methylquinazolin-5-oxy)ethyl]piperidin-4-ylmethyl}-3,4-dihydro-2H-benzo[1,4]oxazine; and or a pharmaceutically acceptable salt thereof.

8. A process for the preparation of the compound of formula (I) as defined in claim 1 or pharmaceutically acceptable salt thereof, which process comprises:

(a) the coupling of a compound of formula (II):

(II)

wherein A has the same meaning as formula (I) and L is a leaving group, and a compound of formula (III):

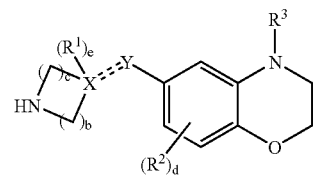

(III)

wherein b, c, d, e, X, Y, $R^1$, $R^2$, $R^3$, and

===== have the same meanings as for formula (I); or (b) for a compound wherein X is nitrogen, the coupling of a compound of formula (IV):

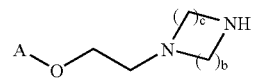

(IV)

wherein A, b and c have the same meanings as for formula (I), and a compound of formula (V):

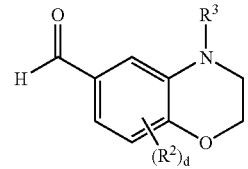

(V)

wherein $R^2$, d, and $R^3$ have the same meanings as for formula (I), and thereafter optionally for process (a) or process (b):

removing any protecting groups and/or
converting the compound of formula (I) into another compound of formula (I) and/or
forming a pharmaceutically acceptable salt.

9. A pharmaceutical composition comprising the compound as defined in claim 1 or pharmaceutically acceptable salt thereof, and a pharmaceutically acceptable diluent, carrier and/or excipient.

10. A process for preparing a pharmaceutical composition comprising mixing the compound as defined in claim 1 or pharmaceutically acceptable salt thereof with a pharmaceutically acceptable diluent, carrier and/or excipient.

11. A method of treating depression or anxiety in mammals including humans, which comprises administering to the sufferer a therapeutically effective amount of the compound as defined in claim 1 or pharmaceutically acceptable salt thereof.

* * * * *